United States Patent
Rabolt et al.

(10) Patent No.: US 6,784,428 B2
(45) Date of Patent: Aug. 31, 2004

(54) APPARATUS AND METHOD FOR REAL TIME IR SPECTROSCOPY

(75) Inventors: John F. Rabolt, Greenville, DE (US); Mei-Wei Tsao, Wilmington, DE (US)

(73) Assignee: UD Technology Corporation, Newark, DE (US)

( * ) Notice: Subject to any disclaimer, the term of this patent is extended or adjusted under 35 U.S.C. 154(b) by 215 days.

(21) Appl. No.: 09/984,137

(22) Filed: Oct. 29, 2001

(65) Prior Publication Data

US 2003/0071216 A1 Apr. 17, 2003

Related U.S. Application Data

(63) Continuation of application No. PCT/US01/30724, filed on Oct. 1, 2001.

(51) Int. Cl.[7] .............................................. G01N 21/35
(52) U.S. Cl. .................................................. 250/339.02
(58) Field of Search .................................... 250/339.02

(56) References Cited

U.S. PATENT DOCUMENTS

| | | | |
|---|---|---|---|
| 3,880,523 A | 4/1975 | Thomas | |
| 4,678,332 A | 7/1987 | Rock et al. | |
| 4,956,555 A | 9/1990 | Woodberry | |
| 5,157,258 A | 10/1992 | Gunning, III et al. | |
| 5,371,358 A | 12/1994 | Chang et al. | |
| 5,377,003 A | 12/1994 | Lewis et al. | |
| 5,444,236 A | 8/1995 | Ludington et al. | |
| 5,491,344 A | 2/1996 | Kenny et al. | |
| 5,519,219 A | 5/1996 | Alexay et al. | |
| 5,528,368 A | 6/1996 | Lewis et al. | |
| 5,539,518 A | 7/1996 | Bennett | |
| 5,828,450 A | 10/1998 | Dou et al. | |
| 6,031,233 A | 2/2000 | Levin et al. | |
| 6,236,508 B1 | 5/2001 | Stapelbroek | |
| 6,355,930 B1 | 3/2002 | Sivathanu et al. | |
| 6,483,112 B1 | 11/2002 | Lewis | |
| 2001/0028036 A1 * | 10/2001 | Thundat et al. ........ | 250/339.02 |

FOREIGN PATENT DOCUMENTS

| | | | | |
|---|---|---|---|---|
| DE | 2938844 A1 * | 4/1981 | ............ | 250/339.02 |

OTHER PUBLICATIONS

S.M. Alawi, T. Krug, H.H. Richardson; *Characterization and Application of an Infrared Linear Array Spectrometer for Time–Resolved Infrared Spectroscopy*, Applied Spectroscopy, vol. 47, No. 10, 1993, p. 1626–1630.

H.H. Richardson, V.W. Pabst, J.A. Butcher, Jr.; *A Novel Infrared Spectrometry Using a Linear Array Detector*, Applied Spectrometry, vol. 44, No. 5, 1990, p. 822–825.

(List continued on next page.)

*Primary Examiner*—Constantine Hannaher
(74) *Attorney, Agent, or Firm*—Larry J. Hume; Connolly, Bove, Lodge & Hutz LLP

(57) ABSTRACT

An apparatus and method capable of providing IR spectral information using IR absorption phenomena requires no moving parts or Fourier Transform during operation. IR spectral information and chemical analysis of a sample in a sample containing functional groups is determined by using an IR source, a sampling accessory for positioning the sample volume, an optically dispersive element, a focal plane array (FPA) arranged to detect the dispersed light beam, and a processor and display to control the FPA, and display an IR spectrograph. Fiber-optic coupling allows remote sensing, and portability, reliability, and ruggedness is enhanced due to the no-moving part construction. Use of the apparatus and method has broad industrial and environmental application, including measurement of thickness and chemical composition of various films, coatings, and liquids, and may also be used in real-time sensing of hazardous materials, including chemical and biological warfare agents.

93 Claims, 7 Drawing Sheets

NON-INTERFEROMETRIC IR SPECTROSCOPY USING NO MOVING PARTS

OTHER PUBLICATIONS

J. Zhao, R.L. McCreery; *Multichannel Fourier Transform Raman Spectroscopy: Combining the Advantages of CCDs with Interferometry*, Applied Spectroscopy, vol. 50, No. 9, 1996, p. 1209–1214, P. Hamm, S. Wiemann, M. Zurek, W. Zinth; *Highly sensitive multichannel spectrometer for subicosecond spectroscopy in the midinfrared*, Institut fur Medizinische Optik Barbarastrasse 16, 80797 Munchen, Germany, Apr. 26, 1994, *Optics Letters*, vol. 19, No. 20, p1042–1044.

CVI Product Template 5 for SM301 PbS Array Spectrometer, www.cvilaser.com/spectral/sm301–929.asp?pcid=349 (downloaded and printed from WWW on Sep. 24, 2001.

M. Stetzle, J. Tuchenhagen, J.F,Rabolt, Novel All–Fibre Optic Fourier Transform Spectrometer with Thermally Scanned Interferometer, Microchim. Acta [Suppl.] vol. 14, pp. 785–787, 1997.

Yamamoto, Kiyoshi: Ishida, Hatsuo: *Interpretation of Reflection and Transmission Spectra for This Films: Reflection*, Applied Spectroscopy, vol. 48, No. 7, 1994, p. 775–787.

Yamamoto, Kiyoshi; Ishida, Hatsuo: *Optical theory applied to infrared spectroscopy*, Vibrational Spectroscopy, 8 (1994), p. 1–36.

Gericke, Arne; Michailov, Alexander V; Huhnerfuss, Heinrich: *Polarized external infrared reflection–absorption spectrometry at the air/water interface: comparison of experimental and theoretical results for different angles of incidence*, Vibrational Spectroscopy, 4 (1993), p. 335–348.

Mendelsohn, Richard; Brauner, Joseph W., Gericke, Arne: *External infrared reflection absorption spectrometry of monolayer films at the air–water interface, Annu,Rec.Phys Chem* 1995, 46, p. 305–333.

Grandbois, Michel; Desbat, Bernard; Salesse, Christian: *Monitoring of phospholipids monolayer hydrolysis by phospholipase A2 by use of polarization–modulated Fourier transform infrared spectroscopy*, Biophysical Chemistry, 88 (2000), p. 127–135.

Grandbois, Michel; Desbat, Bernard; Blaudez, Daniel; Salesse, Christian: *Polyization Modulated Infrared Reflection Absorption Spectroscopy Measurement of Phospholipid Monolayer Hydrolysis by Phospholipase c, Langmuir*, vol. 15, No. 19, 1999, p. 6594–6597.

Flach, Carol R.; Brauner, Joseph W.; Mendelsohn, Richard: *Calcium Ion Interactions with Insoluble Phospholipid Monolayer Films at the A/W Interface, External Reflection–Absorption IR Studies, Biophysical Journal*, vol. 65, Nov. 1993, p. 1994–2001.

Mitchell, Melody L.; Dluhy, Richard A.: *In Situ FT–IR Investigation of Phospholipid Monolayer Phase Transitions at the Air–Water Interface, Journal of the American Chemical Society*, 1988, 110, p. 712–718.

Dluhy, Richard A.; Reilly, Kim E.; Hunt, Rodney D.; Mitchell, Melody L., Mautone, Alan J.; Mendelsohn, Richard: *Infrared spectroscopic investigations of pulmonary surfactant Surface film transitions at the air–water inferface and bulk phase thermotropism*, Biophysical Journal, vol. 56, Dec. 1989, p. 1173–1181.

Dluhy, Richard A: *Quantitative External Reflection Infrared Sprectroscopic Analysis of Insoluble Monolayers Spread at the Air–Water Infrared, The Journal of Physical Chemistry*, vol. 90, No. 7, 1986, p. 1373–1379.

Rabolt, J.F.; Burns, F.C.; Schlotter, N.W.; Swalen, J.D.: *Molecular orientation in this monolayer films by infrared spectroscopy, Journal of Electron Spectroscopy and Related Phenomena*, 30 (1983) p. 29–34.

Flach, Carol R.; Gericke, Arne; Mendelsohn, Richard: *Quantitative Determination of Molecular Chain Tilt Angles in Monolayer Films at the Air/Water Interface: Infrared Reflection/Absorption Spectroscopy of Behenic Acid Methyl Ester, J. Phys. Chem. B.*, vol. 101, No. 1, 1997, p. 58–65.

Hunt, Rodney D.; Mitchell, Melody L.: Dluhy, Richard A.: *The Interfacial Structure of Phospholipid Monolayer Films: and Infrared Reflectance Study, Journal of Molecular Structure*, 214 (1989), p. 93–109.

Gericke, Arne; Mendelsohn, Richard: *Partial Chain Deuteration as an IRRAS Probe of Conformational Order of Different Regions in Hexadccanoic Acid Monolayers at the Air/Water Interface, Langmuir*, 1996, 12, p. 758–762.

Gericke Ame; Fach, Carol R., Mendelsohn, Richard: *Stucture and Orientation of Lung Surfactant SP–C and L–α–Dipalmitoylphosphatidylcholine in Aqueous Monolayers, Biophysical Journal*, vol. 73, Jul. 1997, p. 492–499.

Knobler, Charles M.; Desai, Rashmi C.: *Phase Transitions in Monolayers, Amu. Rec. Phys Chem.* 1992, 43, p. 208–236.

Blaudez, Daniel; Buffeteau, Thierry; Desbat, Bernard; Turlet, Jean Marie: Infrared and Ramam spectroscopies of monolayers at the air–water interface, *Colloid & Interface Science*, 4 (1999), p. 265–272.

Flach, Carol R., Gericke, Ame; Mendelsohn, Richard: *Quantitative Determination of Molecular Chain Tilt Angles in Monolayer Films at the Air/Water Interfaces: Infrared Reflection/Absorption Spectroscopy of Behenic Acid Methyl Ester, J. Phys. Chem.* B, 1997, 101, p. 58–65.

Buffeteau, T.: Blaudez, D.; Pere, E.; Desbat, B.; *Optical Constant Determination in the Infrared of Uniaxially Oriented Monolayers from Transmittance and Reflectance Measurements, J. Phys. Chem B.*, 1999, 103, p. 5020–5027.

Dicko, Awa; Bourque, Helene; Pezolet, Michel: *Study by Infrared spectroscopy of the conformation of dipalmitoylphosphatidylglycerol monolayers at the air–water inferface and transferred on solid substrates, Chemistry and Physics of Lipids*, 96 (1998), p. 125–139.

Flach, Carol R., Gericke, Ame; Keough, Kevin M.W.; Mendelsohn, Richard: *Palmitoylation of lung surfactant protein SP–C alters surface thermodynamics, but not protein secondary structure or orientation in 1,2–dipalmitoylphosphatidylcholine Langmuir films, Biochimica et Biophysica Acta 1416* (1999), p. 11–20.

Flach, Carol R.; Xu, Zhi; Xiaohong, Bi; Brauner, Joseph W.; Mendelsohn, Richard: *Improved IRRAS Apparatus for Studies of Aqueous Monolayer Films; Determination of the Orientation of Each Chain in a Fatty–Acid Homogeneous Ceramide 2*, Applied Spectroscopy, vol. 55, No. 8, 2001, p. 1060–1066.

Blaudez, D.; Boucher, F.; Buffeteau, T.; Desbat, B.; Grandbois, M.; Salesse, C.: *Anisotropic Optical Constants of Bacteriorhodopsin in the Mid–Infrared: Consequence on the Determination of αHelix Orientation, Applied Spectroscopy*, vol. 53, No. 10, 1999, 1299–1304.

Sahai, H.; Umemure, J.; *Molecular Orientation in Langmuir Films of 12–Hydroxysteam Acid Studied by Infrared External–Reflection Spectroscopy*, Langmuir, 1998, 14, 6249–6255.

Baszkin, Adam; Norde, Willem, editors: Physical Chemistry of Biological Interfaces, Infrared Spectroscopy of Biophysical Monomolecular Films at Interfaces: Theory and Applications, Marcel Dekker–Publisher, New York, 2000, pp. 716–747 (and summary bibliographic sheet).

T. Buffeteau, E. Le Calvaz, S. Castano, B. Desbat, D. Blaudez, and J. Dufourcq Anisotropic Optical Constants of a–Helix adn B–Sheet Secondary Structures in the Infrared, American Chemical Society, Washington, DC, Feb. 2000, pp. 1–6 (and summary bibliographic sheet).

* cited by examiner

FIG. 1 – FOURIER TRANSFORM IR (FTIR) MICHELSON INTERFEROMETER (BACKGROUND ART)

INTERFEROMETRIC SPECTROPSCOPY USING NO MOVING PARTS
(BACKGROUND ART)

NON-INTERFEROMETRIC IR SPECTROSCOPY USING NO MOVING PARTS

FIG. 4 – PELLIN-BROCA PRISM IMPLEMENTATION

ZnSe REFRACTIVE INDEX DISPERSION AND OPTICAL REFRACTION
PELLIN-BROCA PRISM IMPLEMENTATION

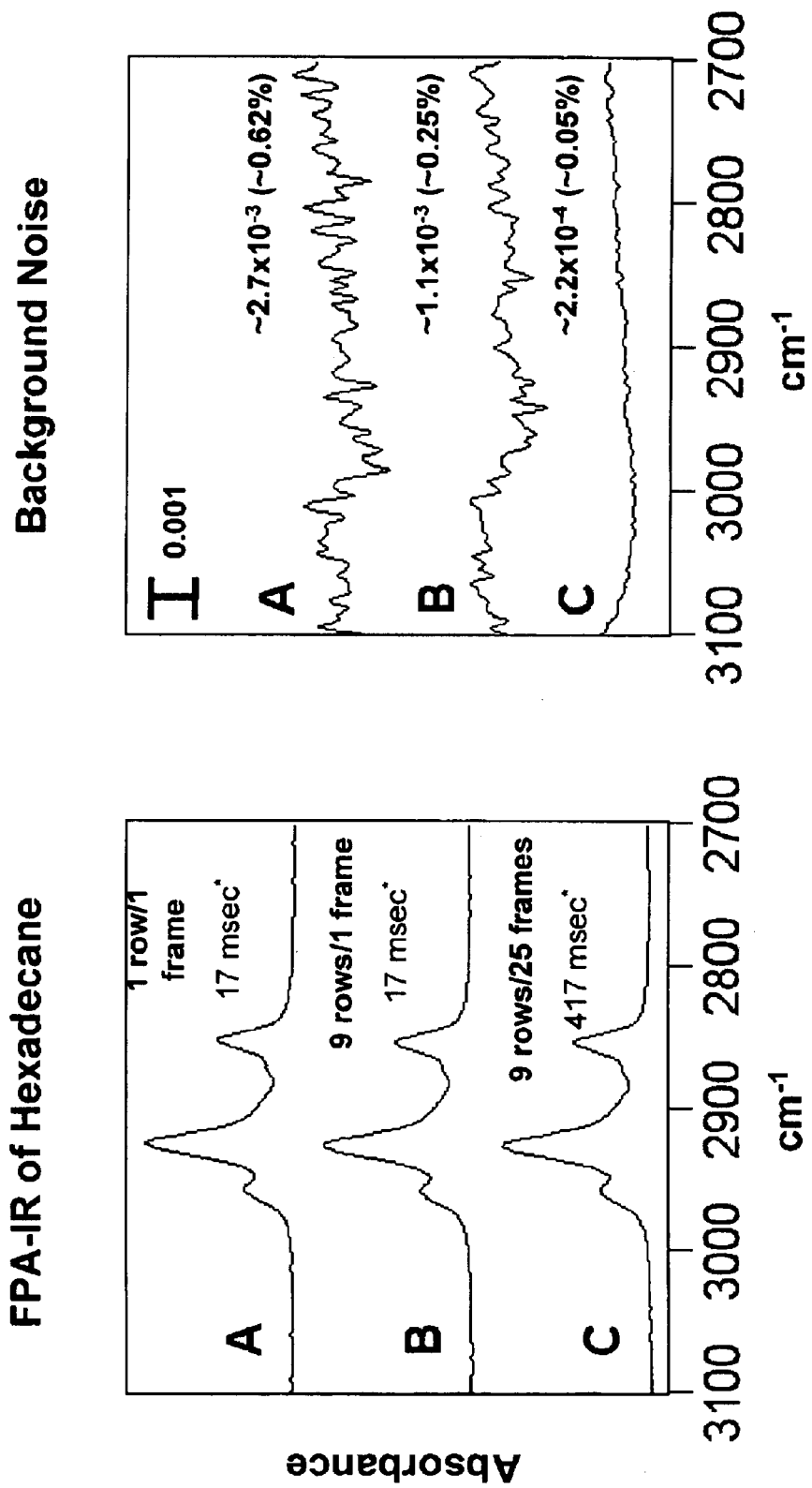
FIG. 6 – NOISE AND SIGNAL AVERAGING

FIG. 7 – FPA IR RESOLUTION
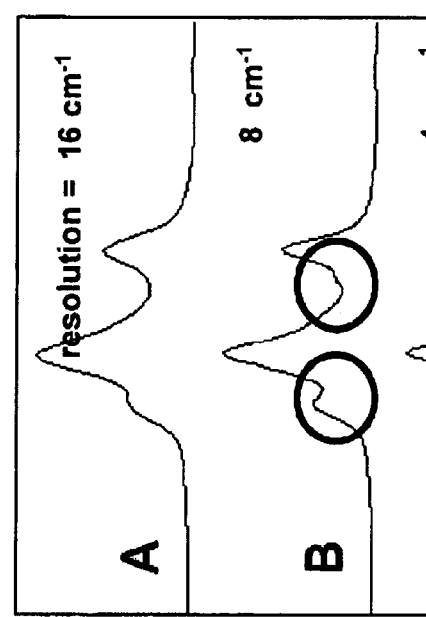
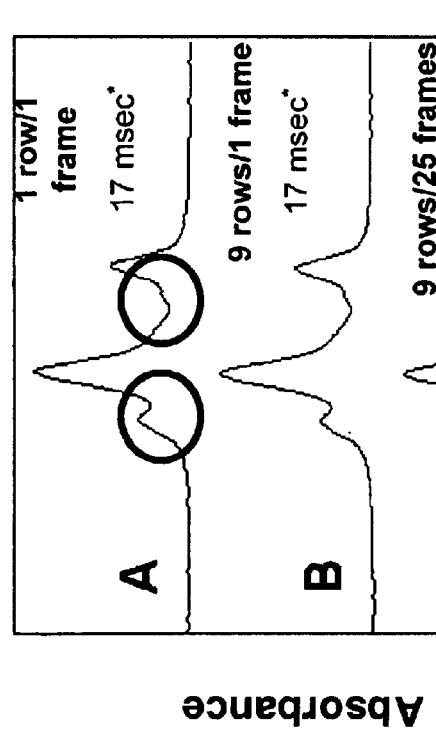
*This is total aquisition time (integration time = 1.5 msec).
FPA-IR: Experimental ≈ 7 cm$^{-1}$ (Theoretical ≈ 5 cm$^{-1}$)

APPARATUS AND METHOD FOR REAL TIME IR SPECTROSCOPY

CROSS-REFERENCE TO RELATED APPLICATIONS

This application is a continuation under 35 U.S.C. §120 of PCT International Application of Rabolt et at. entitled "Apparatus and Method for Real-Time IR Spectroscopy", serial number PCT/US01/30724 filed on Oct. 1, 2001, the entire contents of which are incorporated by reference herein.

GOVERNMENT LICENSE RIGHTS

The United States Government has rights in this invention as provided for by National Science Foundation (NSF) Grant No. 0076017.

TECHNICAL FIELD OF THE INVENTION

This invention relates generally to an apparatus and method for determining an IR spectrum of a sample material. More particularly, the disclosed invention relates to spectroscopically determining the IR spectrum of a sample using an apparatus and method that operate in real-time, and which do not require the use of any moving parts. Still further, the apparatus and method of the disclosed invention do not require extensive mathematical transformation of the detected spectral information to analyze the composition of the sample material.

The disclosed invention has industrial applicability to, for example, a real-time method to monitor manufacturing processes. Such processes include, but are not limited to measurement of thickness, chemical structure, and orientation of coatings on surfaces (solid, liquid, chemically bound, physically adsorbed). These measurements include, but are not limited to those made on biological materials, polymers, superconductors, semiconductors, metals, dielectrics, and minerals. Further applicability is found to a real-time apparatus and method to measure and detect a chemical species present in a chemical reaction involving various processing of materials in any of a gaseous, liquid, or solid state.

BACKGROUND OF THE INVENTION

As industry continues on its path of cost reductions in core technologies, more emphasis will be placed on the optimization of processes and performance. This retrenchment will necessitate the development and introduction of a whole new class of sophisticated instrumentation that is portable, rugged, reliable, and capable of operation over long periods of time in an aggressive industrial or other non-laboratory environment.

Spectrometric techniques are often used in analysis of materials. Classically, spectroscopy is the measurement of the selective absorption, emission, or scattering of light (energy) of specific colors by matter. Visible white light can be separated into its component colors, or spectrum, by a prism, for example. The principal purpose of a spectroscopic measurement is usually to identify the chemical composition of an unknown material, or to elucidate details of the structure, motion, or environmental characteristics (e.g., internal temperature, pressure, magnetic field strength, etc.) of a "known" material or object. Spectroscopy's widespread technical importance to many areas of science and industry can be traced back to nineteenth-century successes, such as characterizing natural and synthetic dyes, and determining the elemental compositions of stars.

Modern applications of spectroscopy have generalized the meaning of "light" to include the entire range or spectrum of electromagnetic radiation, which extends from gamma- and x-rays, through ultraviolet, visible, and infrared light, to microwaves and radio waves. All these various forms (or wavelength ranges) of electromagnetic radiation have their own characteristic methods of measurement. These different methods give rise to various types of spectroscopic apparatus and techniques that are outwardly very different from each other, and which often rely upon difference physical phenomena to make measurements of material characteristics. Further, the various experts and other researchers in these diverse fields, more often than not, do not cross the technical boundaries between these areas of specialization, as different and somewhat compartmentalized knowledge bases and "rules of thumb" are used.

The use of infrared (IR) is one of numerous spectroscopic techniques for analyzing the chemistry of materials. In all cases, spectroscopic analysis implies a measurement of a very specific wavelength of light energy, either in terms of the amount absorbed or reflected by the sample in question, or the amount emitted from the sample when suitably energized.

In the case of IR, an absorption form of spectrometric analysis is relied upon. IR radiation does not have enough energy to induce transitions between different electronic states, i.e., between molecular orbitals, as seen with ultraviolet (UV), for example. Unlike atomic absorption, IR spectroscopy examines vibrational transitions within a single electronic state of a molecule, and is not concerned with specific elements, such as Pb, Cu, etc. Such vibrations fall into one of three main categories, i.e., stretching, which results from a change in inter-atomic distance along the bond axis; bending, which results from a change in the angle between two bonds; and torsional coupling, which relates to a change in angle and separation distance between two groups of atoms. Almost all materials absorb IR radiation, except homonuclear diatomic molecules, e.g., $O_2$, $H_2$, $N_2$, $Cl_2$, $F_2$, or noble gases.

IR typically covers the range of the electromagnetic spectrum between 0.78 and 1000 $\mu$m. Within the context of IR spectroscopy, temporal frequencies are measured in "wavenumbers" (in units of $cm^{-1}$), which are calculated by taking the reciprocal of the wavelength (in centimeters) of the radiation. Although not precisely defined, the IR range is sometimes further delineated by three regions having the wavelength and corresponding wavenumber ranges indicated:

| | | |
|---|---|---|
| "near-IR": | 0.78–2.5 $\mu$m | 12800–4000 $cm^{-1}$; |
| "mid-IR" | 2.5–50 $\mu$m | 4000–200 $cm^{-1}$; and |
| "far-IR" | 50–1000 $\mu$m | 200–10 $cm^{-1}$ |

For a molecule to absorb IR, the vibrations or rotations within the molecule must cause a net change in the dipole moment of the molecule. The alternating electric field of the incident IR radiation interacts with fluctuations in the dipole moment of the molecule and, if the frequency of the radiation matches the vibrational frequency of the molecule, then radiation will be absorbed, causing a reduction in the IR band intensity due to the molecular vibration.

An electronic state of a molecular functional group may have many associated vibrational states, each at a different energy level. Consequently, IR spectroscopy is concerned with the groupings of atoms in specific chemical combinations to form what are known as "functional groups", or molecular species. These various functional groups help to determine a material's properties or expected behavior by the absorption characteristics of associated types of chemical bonds. These chemical bonds undergo a change in dipole moment during a vibration. Examples of such functional groups and their respective energy bands include, for example, hydroxl (O—H) (3610–3640 cm$^{-1}$), amines (N—H) (3300–3500 cm$^{-1}$), aromatic rings (C—H) (3000–3100 cm$^{-1}$), alkenes (C—H) (3020–3080 cm$^{-1}$), alkanes (C—H) (2850–2960 cm$^{-1}$), nitrites (C=-N) (2210–2260 cm$^{-1}$), carbonyl (C=O) (1650–1750 cm$^{-1}$), or amines (C—N) (1180–1360 cm$^{-1}$). The IR absorption bands associated with each of these functional groups act as a type of "fingerprint" which is very useful in composition analysis, particularly for identification of organic and organometallic molecules.

By knowing which wavelengths are absorbed by each functional group of interest, an appropriate wavelength can be directed at the sample being analyzed, and then the amount of energy absorbed by the sample can be measured. The intensity of the absorption is related to the concentration of the component. The more energy that is absorbed, the more of that particular functional group exists in the sample. Results can therefore be numerically quantified. Further, the absence of an absorption band in a sample can often provide equally useful information.

Intensity and frequency of sample absorption are depicted in a two-dimensional plot called a spectrum. Intensity is generally reported in terms of absorbance, the amount of light absorbed by a sample, or percent transmittance, the amount of light that passes through it. In IR spectroscopy, frequency is usually reported in terms of wavenumbers, as defined above.

Infrared spectrometers may be built using a light source (e.g., the sun), a wavelength discriminating unit or optically dispersive element such as a prism, for example, and a detector sensitive to IR. By scanning the optically dispersive element, spectral information may be obtained at different wavelengths. However, one drawback to this approach is the moving parts associated with the required scanning operation. Such moving parts inherently limit the ruggedness and portability, for example, of such a device.

More recently, a Michelson interferometer has been used to generate a so-called interferogram in the IR spectrum, which later is subjected to Fourier transform processing such as a fast Fourier transform (FFT) to yield the final spectrum. In the IR range, such spectrometers are called FTIR interferometers, and the first commercially available appeared in the mid 1960's. A representation of an FTIR interferometer is provided in FIG. 1.

The key components of FTIR interferometer 100 are IR source 110, interferometer (130, 140, 150), and IR detector 160. FTIR interferometer 100 provides a means for the spectrometer to measure all optical frequencies transmitted through sample 120 simultaneously, modulating the intensity of individual frequencies of radiation before detector 160 picks up the signal. Typically, moving mirror arrangement 150 is used to obtain a path length difference between two (initially) identical beams of light. After traveling a different distance than a reference beam, the second beam and the reference beam are recombined, and an interference pattern results. IR detector 160 is used to detect this interference pattern.

The detected interference pattern, or interferogram, is a plot of intensity versus mirror position. The interferogram is a summation of all the wavelengths emitted by the sample and, for all practical purposes, the interferogram cannot be interpreted in its original form. Using the mathematical process of Fourier Transform (FT), a computer or dedicated processor converts the interferogram into a spectrum that is characteristic of the light either absorbed or transmitted through sample 120.

The invention of FT spectroscopy has proven to be one of the most important advances in modern instrumentation development in the 20th Century. Optical spectroscopy utilizing the interference of light has made fast, sensitive detection of molecular vibration/rotation possible due to the large throughput and multiplex advantages provided by FT instrumentation. In Nuclear Magnetic Resonance (NMR) and mass spectroscopy where high-resolution spectra are required, FT instrumentation has also prevailed as the state of the art.

The same technological innovations that have made FT instruments those of choice for a generation of spectroscopists, however, have also made them extremely sensitive to their operating environment. For these reasons, FT interferometers are mostly limited to laboratory conditions which require the use of an optical bench to prevent vibration, and which also require stringent environmental controls to control temperature variations that adversely affect the interferogram by thermally inducing pathlength differences. While this type of scanning approach is workable, the signal-to-noise-ratios (SNR) obtainable often requires substantial signal averaging of multiple interferograms, thus making FTIR systems inherently slow, with reduced speed and lower reliability resulting from the numerous moving parts of these systems.

In spectroscopy, resolution is a measure of the ability to resolve or differentiate two peaks in the spectrum, where high resolution corresponds to a small wavenumber difference between the peak positions, and low resolution is associated with a larger wavenumber difference between the peak positions. Fourier Transform interferometers are capable of extremely high resolution, on the order of $\frac{1}{1000}^{th}$ cm$^{-1}$, depending on the amount of possible movement of the mirror, or the pathlength difference that can be generated by the particular apparatus. "Low" resolution is generally considered to be in the range of 16–32 cm$^{-1}$, although no bright-line demarcation between "low" and "high" resolution exists, as resolution is chosen based on the required measurement and specific application. For typical chemical analysis and identification associated with FTIR, "high" resolution of 8 cm$^{-1}$ or better is common. Otherwise, chemical information is lost if the resolution is too low, as adjacent peaks identified with a particular chemical bond or vibration state may be "smeared" together and rendered indiscernible if a lower resolution is used.

The need for thermal stability, mechanical vibration isolation, and stringent optical alignment has put severe constraints on where and how FT instruments can be used and, in particular, has limited the portability of such instruments. If discussion is limited to FTIR interferometers, then an examination of the specific technology used in currently available instruments reveals where some of the shortcomings can be found. Table 1 compares the four most commonly used techniques for the operation of an optical interferometer, and their limitations.

TABLE 1

Common FTIR Interferometer Designs and their Limitations

| Operating Technologies | Limitations |
| --- | --- |
| Air-Bearings | Requires stable supply of clean, dry air and a tightly leveled travel plane for the moving mirror. Low tolerance for vibration. |
| Magnetic Coils | Requires highly regulated power supplies. Low tolerance for vibration. |
| Piezo Stacks | Limited travel range. High voltage power supplies needed to operate the piezo elements. |
| Mechanical/Piezo Hybrid | Requires large mechanical structures and complicated feedback system for piezo element operation. |

FTIR has been applied to a variety of studies in industry, government, and academic laboratories, and has resulted in a major improvement upon conventional methods of performing analysis on a variety of samples. However, it has become clear that the moving mirror mechanism in a traditional interferometer has limited the design and construction of a more compact and portable FTIR. One potential solution attempted by Stelzle, Tuchtenhagen, and Rabolt ("Novel All-fibre-optic Fourier-transform Spectrometer with Thermally Scanned Interferometer"), was to construct an all-fiber-optic FT Spectrometer, which had no moving parts, and which was used to perform infrared spectroscopy.

In this feasibility study, an attempt was made to build an interferometer in the near-IR (10000–5000 $cm^{-1}$) range using fiber optics. Two carefully measured and cleaved optical fibers were used as the two light channels, or optical paths, with one fiber kept at ambient temperature while the other fiber was heated/cooled repeatedly. The resulting optical path difference (OPD) between the two fiber channels due to changes in both the length and the refractive index of the heated/cooled fiber causes interference in the combined channel. The heating/cooling cycle was used to generate an OPD of 3 cm, thus producing an interferogram with the power spectrum calculated accordingly.

However, the interference of two light beams in the optical fibers under different thermal and mechanical conditions turned out to be very complex. In contrast to the traditional Michelson interferometer, whose only source of optical path length difference comes from the geometric pathlength resulting from the moving mirror, a fiber-optic interferometer responds to any mechanical or thermal changes of the operating environment, which causes a scrambling or loss of the phase information necessary for interference to occur. It was concluded that although the fiber optics concept is a good one, a more prudent plan for a no-moving parts IR instrument had to be developed.

In surveying the literature, it became apparent that, without regard to the band of interest, e.g., visible, near-IR, or IR, other approaches to the construction of an FT interferometer with no-moving parts had also been attempted, as depicted in FIG. 2. Such approaches used either a linear array detector or a focal plane array (FPA) to collect interferograms. These designs involved the projection of the center portion of the interferogram onto the detector, and then used the "imaged" interferograms to calculate the power spectra after Fourier Transform processing. One difficulty of these conventional techniques is that the array detector size, its dynamic range, and the limited range of spectral response available limited the range of the interferograms that could be captured by the array detector.

In addition, even without moving parts, these approaches still rely upon calculation-intensive Fourier Transform processing to derive the power spectrum. Hence, there is still a need for a rugged, non-interferometric, no-moving part spectrometer in the mid-IR range.

Aside from Fourier Transform spectroscopy, spectroscopy based on dispersion also provides a possible implementation. In this approach, an optically dispersive element, such as a prism or diffraction grating, is used to separate the spectral frequencies present in the incident light radiation. The dispersive element was then rotated, in order to allow the various wavelengths present in the incident light to be detected.

IR spectroscopy based on dispersion became obsolete in most analytical applications in the late 1970's due to its slow scan rate and lower sensitivity. It is well known that the scanning mechanism in a dispersive spectrometer, e.g., a moving prism, intrinsically limits both its ruggedness and optical throughput. The need for scanning comes from the fact that point detection of photons was the only available method at that time, and this was especially true in the IR range of the spectrum. Today, however, array detectors in the visible and near-IR range are widely available for area detection of photons. Charge-coupled-devices (CCD) capable of >80% quantum efficiency (QE) in the visible range have been made and utilized in many applications, such as the visible/near-IR camera aboard the Hubble Space telescope. As a result of this progress, CCD-based high performance spectrograph systems in the visible and near-infrared range can now be purchased through commercial suppliers. These systems provide alternatives to traditional FT interferometers.

However, the range of scientific problems which could now benefit from IR investigations has increased significantly, and applications involving samples which may change their position in the beam (e.g., vibrate or oscillate) while the spectrum is being recorded can not be routinely addressed using conventional FTIR instruments. The scanning architecture of FTIR instruments and the resulting modulation of the different optical frequency components can become modified further by a sample whose position fluctuates, and this can render the spectral information useless.

Hence, the need for a non-scanning instrument with convenient delivery and detection of IR radiation could never be stronger. For example, applications requiring on-line studies of micro mechanical deformation in polymer thin films during processing, in situ structural studies of aging in Light Emitting Diodes (LEDs), and the monitoring of inorganic (silicon, SiN, etc.) thin film growth on flexible polymer substrates would all benefit from an IR instrument with no moving parts, which as a consequence, will also be robust and portable. Such a portable instrument would facilitate materials research by providing a powerful new tool for thin film studies, especially those with fluctuating sampling geometries or in a remote sample location.

Further advantages for such a non-scanning, real-time instrument in the IR range could be found in environmental monitoring, including monitoring near military or civilian personnel during potential chemical or biological warfare attacks, due to the complex chemical compositions in such agents which show strong IR absorbance, and thus could be readily identified.

In spite of the inroads made in spectroscopy by spectrographs in the visible and near-infrared range due to the progress in CCD detectors mentioned previously, FT instrumentation still remains dominant in spectroscopy in the mid to far-infrared range and, therefore, instruments in this range are still extremely limited by the operating environment of the interferometer.

What is needed, then, is a robust, compact, and portable instrument in the IR range to address specific applications where sample fluctuations cause significant deterioration of the S/N in conventional FTIR spectra.

What is further needed is a portable and reliable IR spectroscope with no moving parts, and which is based upon IR focal plane array (FPA) technology.

Still what is further needed is a real-time, sensitive and relatively high-resolution apparatus and method for IR spectroscopic materials analysis, which does not rely upon interferometry or a calculation-intensive Fourier Transform approach, and which is relatively insensitive to harsh environments, including high vibration and wide temperature variations.

SUMMARY OF THE INVENTION

The present invention solves many of the aforementioned problems of providing a robust, high-resolution and sensitive apparatus and method for determining an IR spectrum of a sample material, without the use of moving parts, or calculation-intensive Fourier Transform interferometric techniques.

A first embodiment of the present invention includes an apparatus for determining an IR spectrum of a sample material based upon IR FPA technology to capture the IR spectral information, without utilizing a scanning mechanism, or any moving parts, and without the use of Fourier Transform signal processing.

An IR source is passed through a sample volume, where at least some of the IR energy is absorbed in the sample volume. The resulting IR signal is optically dispersed to spread the IR light into its respective wavelength components, and projected onto an IR detector having a plurality of detection elements. The detector output is further processed for display and analysis without interferometric techniques.

In a second embodiment, one or more optical fibers are used to couple the IR source through a sample volume, and into an optically dispersive element, and also into an IR detector. Such an embodiment may be used, for example, in remote-sensing applications, where the phenomena being evaluated are remotely located from the apparatus, particularly the IR detector. In an environmental application, which monitors smokestack emissions, for example, the sample volume to be analyzed may be hundreds of meters in the air. Fiber optical cabling may be used, as may telescopic optics to bring the experiment to the sensor.

In a first aspect of the first embodiment, an InSb focal plane array (FPA) is used to detect absorptions in the 3–5 μm range and, in a second aspect of the first embodiment, a microbolometer-based FPA is utilized for the 7–13 μm range. In yet another aspect of the first embodiment, an HgCdTd (MCT) array, or other InSb array having a wider or different spectral response may be used.

Signals from the samples can be collected by either of two methods. Signal collection by direct lens coupling may be used by coupling the signals into the spectrometer through an aperture. Alternatively, the coupling is also accomplished through the use of mid-IR optical fibers.

Use of optical fibers provide flexibility in placement of the apparatus, and allow remote sensing of, for example, smokestacks, and also allow easier implementation of multiple channel detection and chemical analysis.

The apparatus and method of the present invention does not require moving parts to determine spectral information. The method and apparatus are, consequently, well adapted to relatively harsh environments, such as, for example, high vibration environments in a manufacturing plant.

The method may also be used in various industrial applications to measure and detect the thickness, either in transmission or reflection mode, the chemical structure and orientation of coatings/films (solid, liquid, chemically bound, physically adsorbed) on liquid surfaces, including but not limited to water, oil and other solvents, and also to measure the thickness, orientation and chemical structure of films electrochemically deposited on solid substrates, including but not limited to metals and semiconductors.

BRIEF DESCRIPTION OF THE DRAWINGS

The features and advantages of the invention will be more readily understood upon consideration of the following detailed description of the invention, taken in conjunction with the accompanying drawings in which:

FIG. 6 demonstrates representative noise and signal averaging achievable by the disclosed invention; and FIG. 7 compares results of the disclosed invention with a conventional FTIR interferometer.

DESCRIPTION OF PREFERRED EMBODIMENTS

Figure 1:
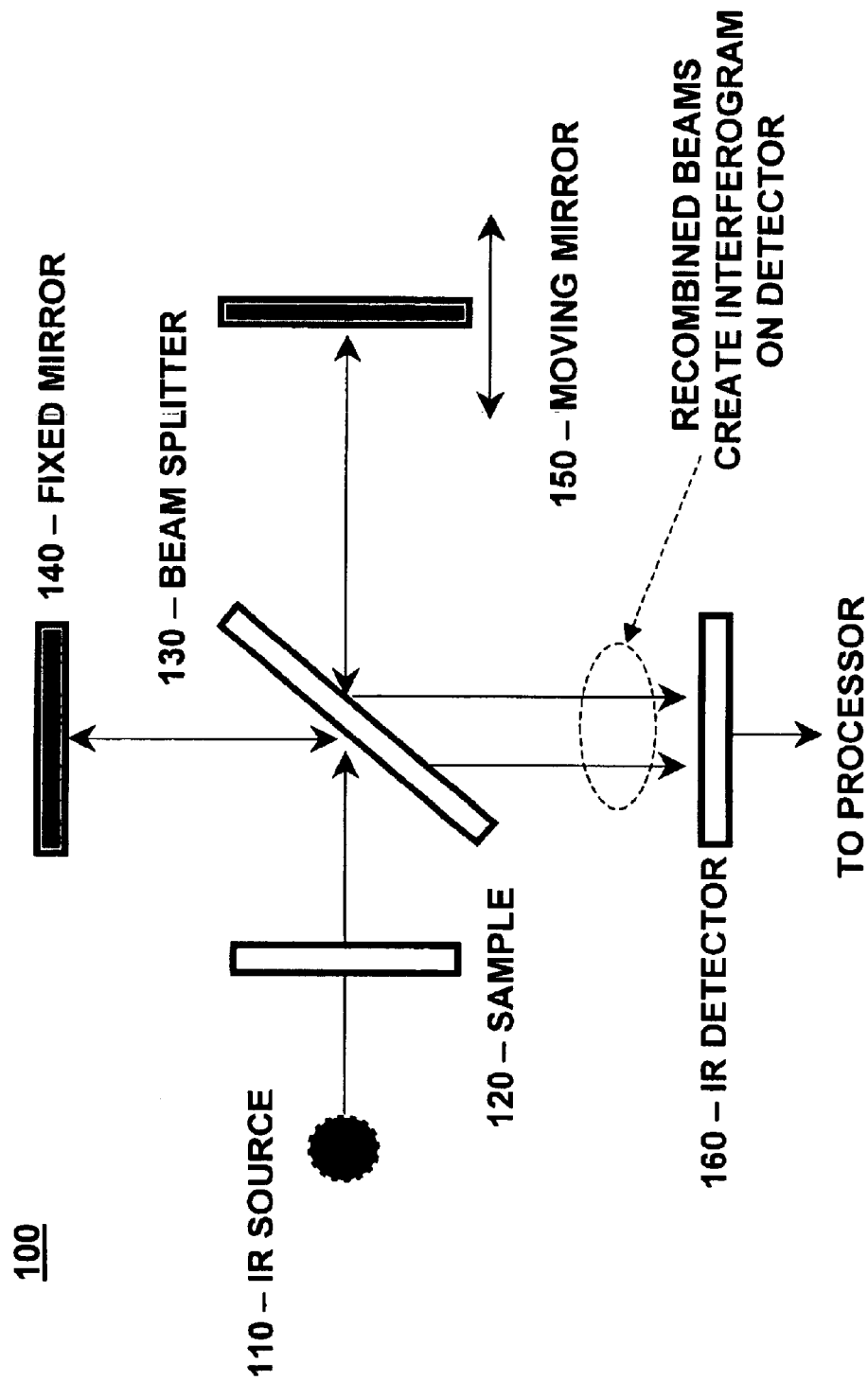
FIG. 1 provides a representation of a conventional FTIR interferometer.
Figure 2:
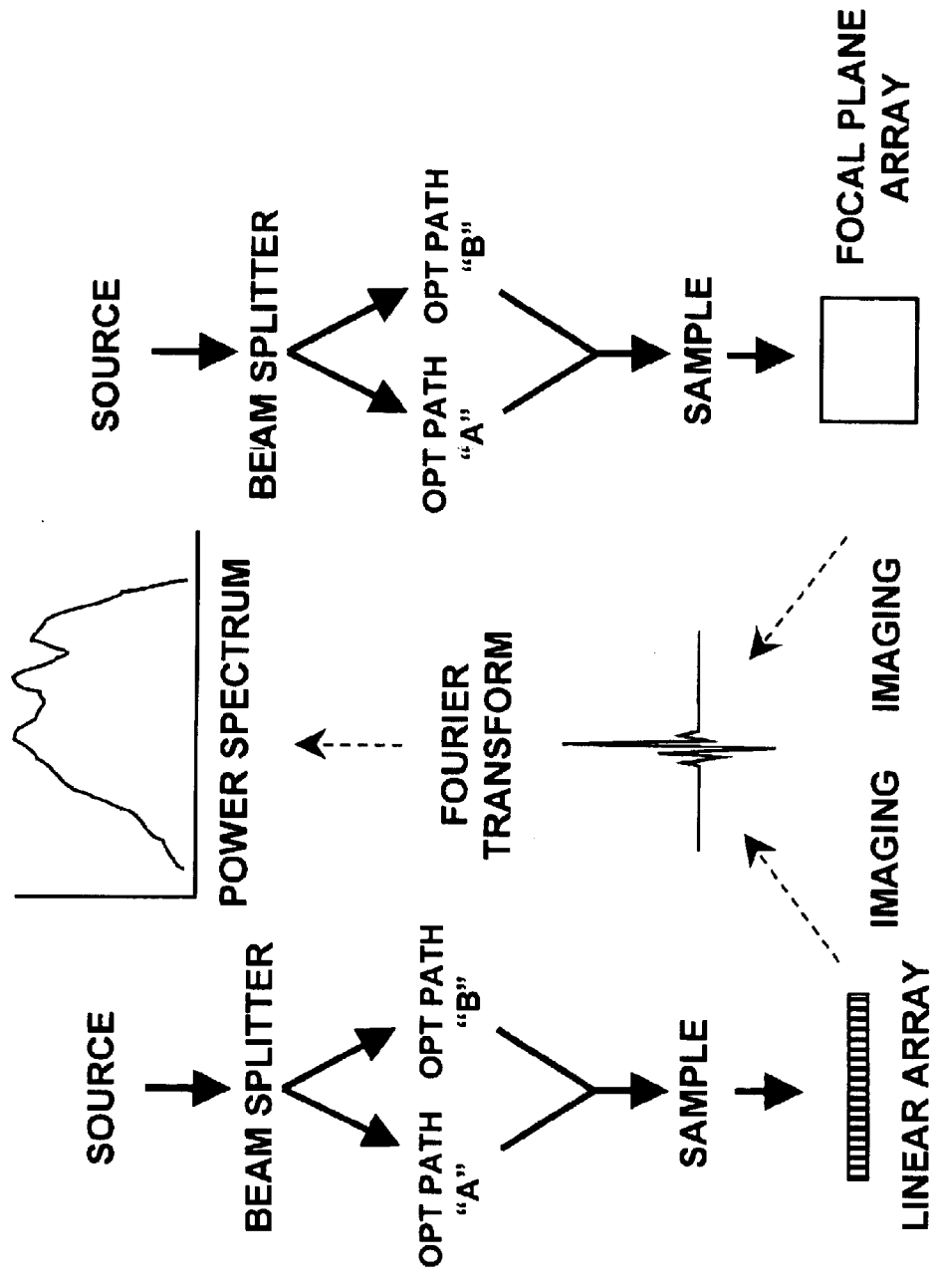
FIG. 2 provides two different schemes used for conventional interferometry based on Fourier Transform, but which do not require moving parts to generate a difference in optical path length.
Figure 3:
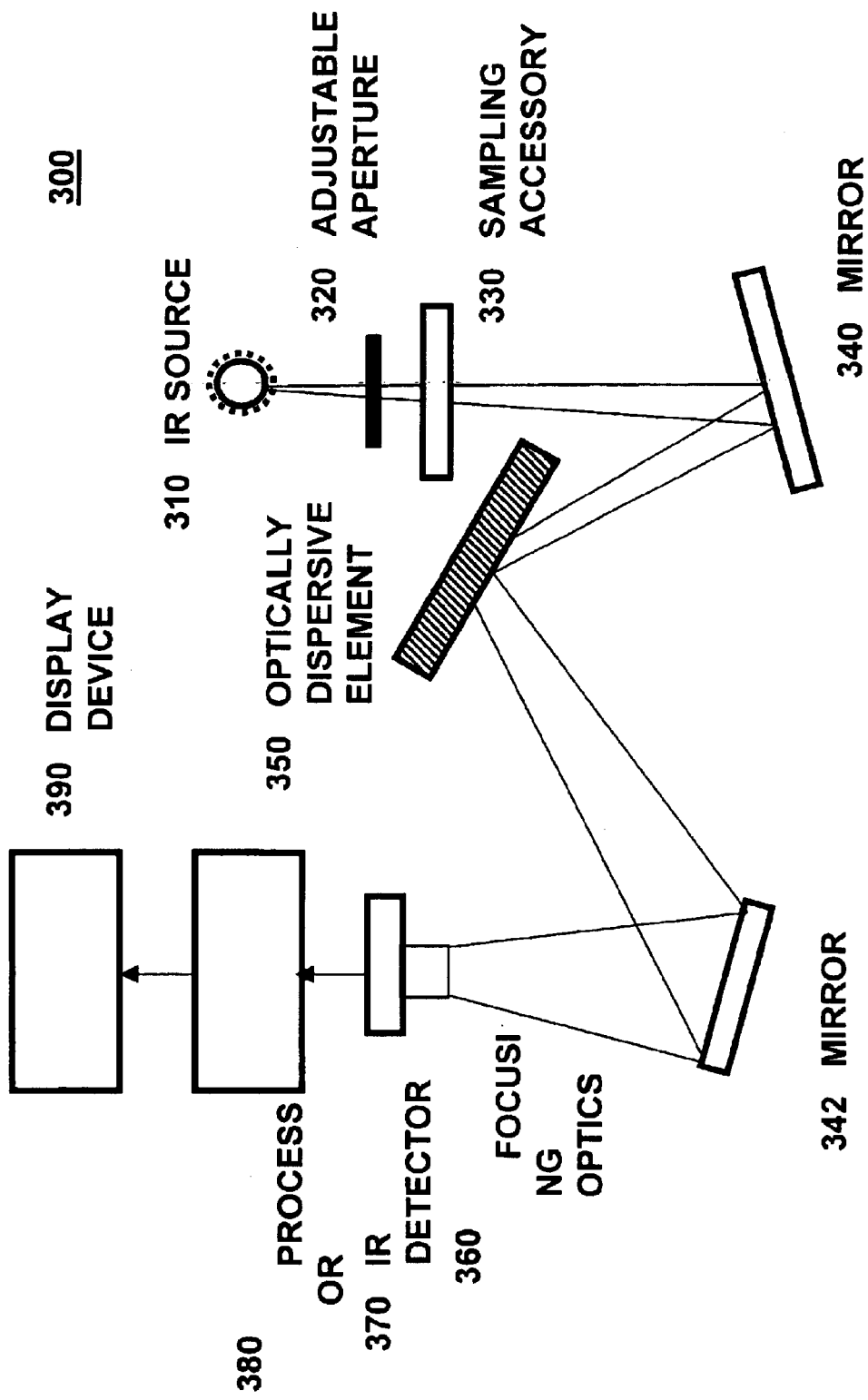
FIG. 3 depicts one embodiment of the present invention in which non-interferometric IR spectroscopy is accomplished using no moving parts.

The first embodiment will be explained with reference to FIG. 3. Apparatus 300 includes an IR light source 310, which may be any common IR light source, including, for example, tungsten lamps, Nernst glowers, or glowbars or, in some applications, IR radiation from the sun may be used. In a preferred embodiment, the IR source may be a IR Emitter with ZnSe window, manufactured by Cal-Sensors, for example. Ideally, IR source 310 has a "flat" or uniform intensity across the IR spectrum, or at least a portion of the IR spectrum. However, if IR source 310 is not uniform, such non-uniformity may be accounted for during the analysis process.

Adjustable aperture 320 is used, at least in part, to establish the resolution of the apparatus, i.e., a smaller-sized opening provides higher resolution. Adjustable aperture 320 may be a circular iris or, in a preferred embodiment, an adjustable rectangular slit, having a length dimension, for example, of approximately 1 cm, and an adjustable width of 0–2 mm. Such a slit is manufactured by RIIC, as model WH-01.

Sampling accessory 330 positions the sample volume, which contains a sample to be analyzed, in the optical path. Sampling accessory 320 may be, in a preferred embodiment, a simple sample holder, which merely positions a small sample volume of material to be sampled, e.g., polymer film, near IR source 310, or it may comprise a more elaborate sampling volume arrangement known and used for sampling gases.

Gases, which have a lower density than solids or liquids, may require such a more elaborate sampling accessory having a set of mirrors or other suitable arrangement (not shown) to provide for multiple passes of the IR source through the sample volume. Such multiple passes are useful in ensuring that sufficient optical density is achieved for the IR absorption phenomena to be reasonably measured. Multiple pass arrangements may also be used, in other embodiments, to monitor smokestack emissions, or to monitor hazardous chemical fumes or vapors in laboratory, military, or industrial environments.

Sampling accessory 330 could also comprise optics including a telescope or microscope arrangement, or coupling to a single optical fiber or bundle of optical fibers.

Further, apparatus 300 may include a plurality of sampling accessories (not shown) that may be used, along with appropriate beam splitting optics, to pass a portion of an emission from IR source 310 through each of the plurality of sampling accessories.

Optically dispersive element 350 receives a portion of an emission from IR light source 310 that is passed through the sample volume. The entire IR spectrum, representative of IR source 310, may not be passed through the sample volume because of the absorption of one or more IR wavelengths in the sample volume within sampling accessory 330. The non-absorbed IR wavelengths then interact with optically dispersive element 350 to form a dispersed light beam, which separates or spreads, in one direction, the wavelengths present in the IR light exiting sampling accessory 330.

Optically dispersive element 350 may be, in one embodiment, a ruled diffraction grating having, for example, 300 lines per mm. Such a grating is manufactured, for example, by SPEX, as model 300 g/mm Holographic Grating.

Figure 4:
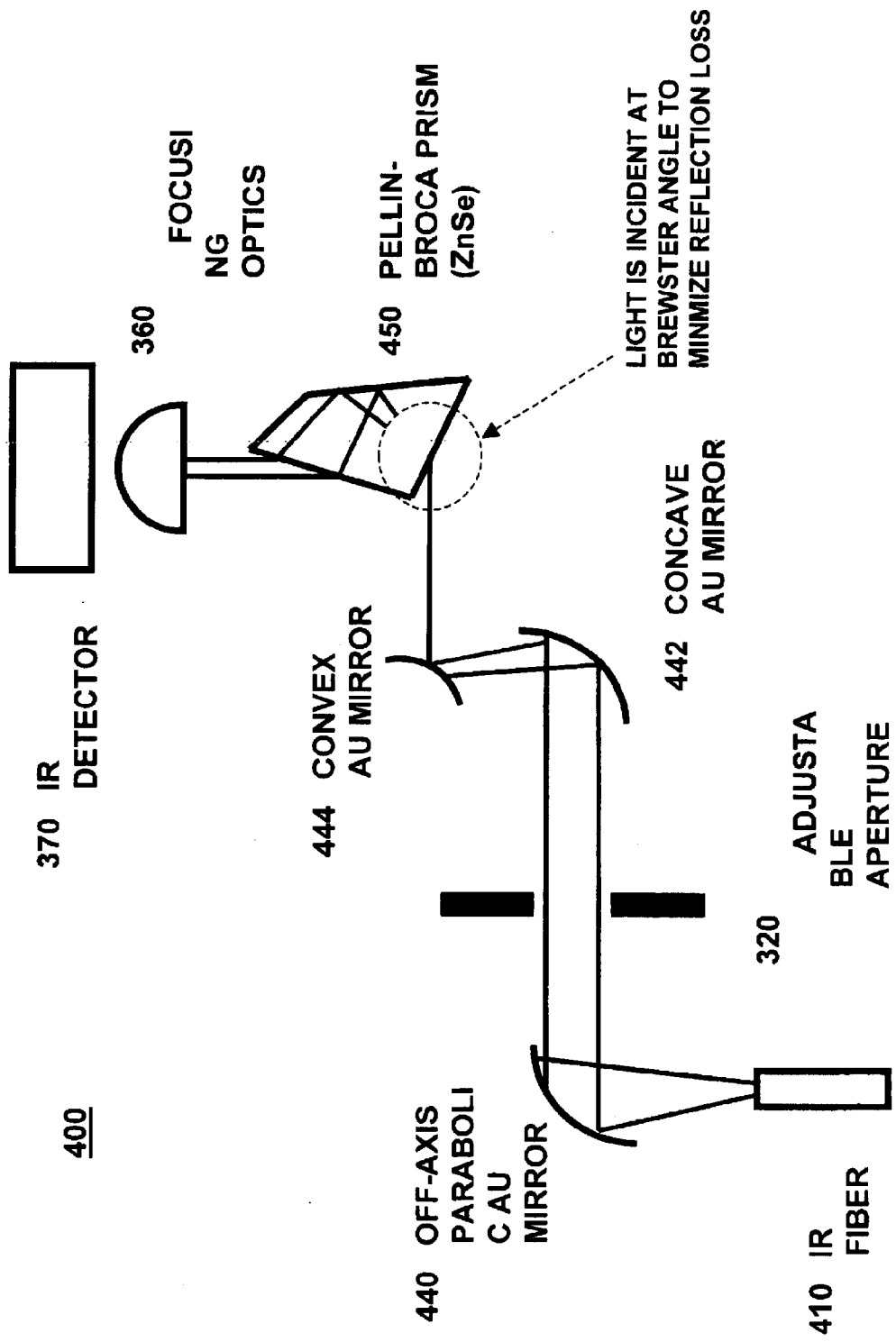
FIG. 4 provides another embodiment using a Pellin-Broca prism as the optically dispersive element, and which shows IR optical fiber being used to couple the light into the apparatus.
Figure 5:
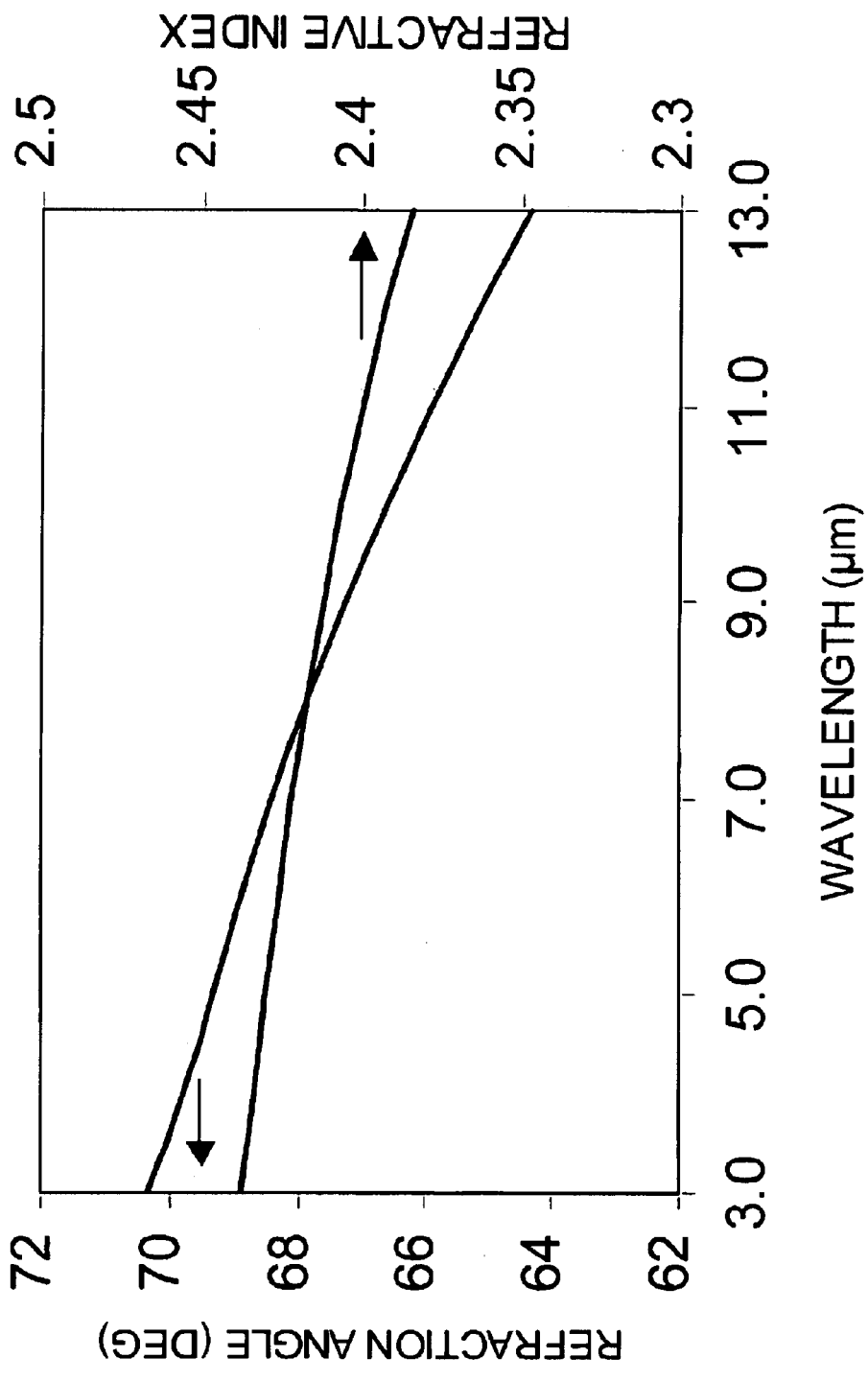
FIG. 5 provides a graph of refractive index dispersion of ZnSe, and optical refraction for an exemplary embodiment of the Pellin-Broca prism of FIG. 4.

In another embodiment, the optically dispersive element may be a prism, as shown in FIG. 4. In a further preferred embodiment, Pellin-Broca prism 450 may be used. In IR wavelengths, the Pellin-Broca prism may be machined from zinc selenide (ZnSe) in order to minimize the material absorption in these IR spectral ranges, and to ensure adequate optical dispersion as a function of wavelength. FIG. 5 provides a graph of refractive index dispersion of ZnSe and optical refraction for an exemplary embodiment of the Pellin-Broca prism of FIG. 4. Apparatus 400 operates similarly to apparatus 300 shown in FIG. 3, however variations in components are optionally present. For example, a light coupling means may include IR fiber 410, which may also include a multi-fiber bundle; off-axis parabolic mirror 440; concave mirror 442; and convex mirror 444. The light being projected by IR fiber 410 may include light coming from the sample volume being illuminated, or the IR fiber may be used to illuminate the sample volume. Focusing optics 370 may be, in this embodiment, a germanium (Ge) condensing lens used to properly project the light emanating from prism 450 onto IR detector 370. The parabolic-shaped mirrors are preferable when using an IR fiber, in order to collimate the cone-shaped fiber output light beam. The Pellin-Broca prism may also be used with the optical coupling and IR source 310 in FIG. 3, as well as in the fiber optic implementation. Conversely, the ruled diffraction grating may be used with fiber optics, assuming that appropriate measures are taken to collimate the conical beam emanating from the fiber, and to couple the light into the system, and onto the diffraction grating, when used as optically dispersive element 350.

Although a diffraction grating can provide adequate resolution for many application, the Pellin-Broca geometry may provide three benefits: (1) optical dispersion is only a function of the refractive indexes at different wavelengths, thus simplifying the optical design; (2) the two-in-one prism design has a very high angular dispersion efficiency, and the approximate 90° beam folding available allows a compact footprint of the optical system to be achieved; and (3) a Brewster angle incident configuration may be utilized in order to maximize the transmission of light at the ambient/ ZnSe interface. The latter is crucial in the IR range where reflection loss is a major concern due to the high refractive index of ZnSe (~2.4).

Besides the Pellin-Broca prism design, special diffractive gratings optimized for mid-IR performance, can theoretically provide similar, if not better throughput and dispersion than a prism approach. However, the dependence of resolution on both the groove number and grating size may put more constraints on the optical design using gratings. Therefore, the use of gratings may be considered where low-cost off-the-shelf gratings with low groove numbers will suffice for the particular application, and in situations where higher resolution is required than can be obtained with prisms.

In either case of using a prism or a diffraction grating, optically dispersive element 350 may be adjustable with respect to an angle of incidence between its surface and incident light which is projected onto the surface. Such an angular adjustment may be used to control the wavelength range, or spectral bandpass that is presented to IR detector 370, discussed below.

Focusing optics 360 couples light from optically dispersive element 350 into IR detector 370 which has a plurality of detection elements arranged at least along a dispersion direction corresponding to the direction of the dispersed light beam. Typically, incident light is projected onto more than one row of pixels, and the projected light from the optically dispersive element may cover 20 pixels. IR detector 370 detects the dispersed light beam from optically dispersive element 350, and provides an output, which is subsequently used to determine the IR spectral information of the sample in the sample volume contained in sampling accessory 330.

In one embodiment, IR detector 370 may be an InSb camera sensitive in the 3–5 $\mu$m wavelength range, for example, Merlin Mid model, manufactured by Indigo Systems. Such a detector includes a 320×256 pixel InSb detector, with 30 micron pixel pitch; a 3.0–5.0 micron changeable cold filter; user selectable frame rates of 15,30 or 60 frame-per-seconds (fps) (minimum); a liquid nitrogen cooled dewar, having a minimum hold time of 4 hours; a noise equivalent temperature difference NE$\Delta$T<20 mK; user selectable integration times from 10 $\mu$s to 16.6 ms; and corrected non-uniformity <0.1%. InSb detectors in this range may also be thermoelectrically cooled to enhance portability.

This particular InSb camera may be controlled via on camera controls or via an RS-232 interface with a vendor supplied Graphical User Interface, or standard Windows® terminal communications program, or commercially available interfaces such as Universal Serial Bus (USB) or IEEE 1394 standard interface. In addition, this camera provides an automatic gain control (AGC) algorithm, adjustable detector gain and bias to allow viewing of both high and low brightness scenes, and data outputs which may include NTSC, S-Video, and 12 bit corrected digital video. In addition, focusing optics 360 may be provided along with IR detector 370; the above-described InSb detector is commercially available with a 25 mm mid-IR lens.

In another embodiment, IR detector 370 may be a microbolometer camera, also manufactured by Indigo Systems as model Merlin Uncooled. This particular camera includes a 320×240 pixel microbolometer detector having 51 micron pixel pitch in a 7.5–13.5 $\mu$m spectral range. User selectable frame rates of 15, 30 or 60 fps (minimum) are available, This device, in contrast to the InSb, camera, is thermoelectrically (TE) stabilized at 313 K has a noise equivalent temperature difference NE$\Delta$T<100 mK; and has user selectable integration times from 1–48 $\mu$s.

This detector array may be controlled in the same manner as for the InSb array, as discussed above. Similar detector gain controls, and data outputs are available, as in the InSb model.

Further, mercury-cadmium-telluride HgCdTe (MCT) arrays show great promise for use as IR detector 370, and have improved sensitivity and bandwidth in comparison to the InSb and microbolometer devices. Presently, such arrays are somewhat difficult to manufacture, and are more expensive than other available IR detectors.

Although both InSb and microbolometer types of detectors may be cooled thermoelectrically, the sensitivity of the InSb FPA is much higher than that of the microbolometer FPA. As a matter of fact, the sensitivity for the InSb FPA identified above is better than a liquid nitrogen-cooled MCT detector commonly used in traditional FTIR. On the other hand, the sensitivity of the state-of-the-art microbolometer-based FPA is still about one order of magnitude lower than that of liquid nitrogen-cooled MCT detector. However, sensitivity at the performance level of a liquid nitrogen-cooled MCT detector is not always necessary and, for many applications, it is possible that the lower sensitivity of the microbolometer FPA will not cause any significant efficiency problem in the apparatus. In addition, the key advantage of using an FPA, when compared to single element detector, is the possibility of vertical binning. By adding the signal from a finite height of pixels, SNR can be significantly improved.

Although IR detector 370 has been described in terms of a focal plane array (FPA) configuration, a linear array detector may also be used as IR detector 370. However, as discussed above, a linear array detector having a plurality of detector elements in the one-dimensional array is not capable of taking advantage of several features that a two-dimensional detector array offers. Such advantages are, for example, vertical "binning" or co-adding of detector array pixel outputs to increase a signal-to-noise (SNR) ratio, and multichannel detection capability using different areas of the FPA for multiple sample analysis. These additional features would not be available with a linear array.

An optical path or light coupling means between the various elements in apparatus 300 may include, in one embodiment, standard IR mirrors 340, 342 of various configurations to couple light from IR source 310, through the sample volume in sampling accessory 320, onto or thru optically dispersive element 330, and onto IR detector 370 through focusing optics 360. Such mirrors may be, for example, 3-inch (~7.6 cm) diameter front surface aluminum mirrors, manufactured by Newport Corporation. Other mirror coatings available for use in the IR band may be, for example, copper or gold.

In another embodiment depicted in FIG. 5, the optical path may include the use of an optical fiber or optical fiber bundle, particularly multimode IR optical fibers, such as, for example, fiber model C1-500 manufactured by Amorphous Materials, Inc. Different sample types and sampling geometry may advantageously allow a mid-IR optical fiber to be incorporated between the source and dispersing element to deliver the IR source to the sample volume, and to provide an optical path for the IR light after absorption in the sample volume to the dispersive element.

Optical fibers with loss below 1 dB/m in the mid-IR range (including the 3–5 or 7–13 $\mu$m range), are commercially available. These multimode fibers offer features such as flexibility and ease-of-use as found in their fiber counterparts in the visible and near-IR range. The thermal and mechanical properties of these optical materials have been improved dramatically over the past decade.

When combining FPA detector and a multichannel fiber bundle, simultaneous measurements of several samples, or the same sample at different locations, become possible. This means that the proposed spectrometer can offer multiple detection channels with a single instrument, therefore dramatically reduce the cost-of-ownership on a per channel basis. In the general design scheme shown in FIG. 4, off-axis parabolic mirror 440 is utilized to collect and collimate the signals from either the entrance aperture or an output end of IR fiber 410 or fiber bundle. An adjustable aperture 420 may be used to control the size of the collimated beam, and subsequent condensing optics 442, 444 are used to couple the signal into the prism. The combination of the beam condensing optics and aperture size determines the f-number of the spectrometer, and therefore the spectral resolution.

Processor 380 may be a special purpose computer adapted specifically for IR spectral processing, and may be implemented in so-called "firmware" or integrated circuits such as a custom application specific integrated circuit (ASIC), or may be a common personal computer (PC). Processor 380 preferably provides control software/hardware for IR detector 370.

In a preferred embodiment using either one of the FPAs discussed above, "Talon Ultra" Data Acquisition System, manufactured by Indigo Systems may be used. Processor 380 may be implemented as a dedicated IR image acquisition station which includes a 500 MHz Pentium® III PC, 256 MB RAM, 12 GB hard drive, Windows® NT 4.0 operating system, IR camera digital interface cable (10 ft, or ~3 m), high speed 16 bit frame grabber, camera interface software, and image analysis software based on Image Pro® 4.0 or equal. Such an exemplary package provides a full range of utilities for processing, measuring, analyzing, and outputting images to capture, study, manipulate, and store images and data from the IR camera.

Display device 390 may be either a standard computer monitor such as a CRT or LCD display, or may be a printing device.

Although this particular exemplary embodiment may use the PC system memory for data acquisition, a special-purpose, dedicated high-speed memory may also be utilized (not shown). For added portability, processor 380 may be incorporated into a laptop or notebook computer, with an integral LCD display.

In an exemplary embodiment, software running on processor 380 preferably provides a wide variety of features such as real-time histograms; real-time digital filtering; real-time frame averaging, a user definable region-of-interest (ROI); full-featured data display, reduction, analysis capability; and Visual Basic-compatible macro language for automating data collection, analysis, and reporting.

In this type of application, "real-time" is preferably considered to be less than one second, from initialization, through sampling and analysis, and is even more preferably considered to be less than 500 ms, and is even more preferable to be less than 20 ms. This type of response time provides favorable results over the conventional scanning and interferometric techniques. Further, "real-time" detection more preferably means the ability to continuously monitor a process as it happens, where the time domain between collected data sets, or duty cycle is, in general, in the 5–100 $\mu$s range.

Additional analysis software may operate in processor 380 to analyze the IR spectral information, and to determine one or more specific functional groups found in the sample volume, e.g., fluorocarbons, hydrocarbons, or complex molecular bonds or "signature" functional groups, such as those found in chemical or biological warfare agents. Further, an alarm, either audible or visual, or both may also be activated if a particular signature functional group or chemical composition is determined to be in the sample volume.

Although some components of apparatus 300 are adjustable to facilitate setup or to provide for optimal data collection, it should be noted that apparatus 300 is capable of determining IR spectral information using no moving parts whatsoever during operation.

The non-interferometric apparatus of the first embodiment is operated to determine an IR spectrum of a sample in a sample volume by providing an IR source; positioning the sample volume in the optical path; passing at least a portion of an emission of the IR source through the sample volume and into the optical path; optically dispersing the at least a portion of an emission of the IR source to form a dispersed IR light beam; detecting the dispersed IR light beam using the plurality of detectors; and non-interferometrically determining the IR spectrum of the sample by evaluating an output from the plurality of detectors. In a more preferred method, a two-dimensional detector array, such as a FPA, for example, is operated, wherein each column of detectors represents a wavelength contained within the dispersed IR light beam, and at least two rows of detector elements are used to improve a SNR of the detected signal.

Before the apparatus may reliably be used, IR source 310 must be calibrated, or preferably at least the spectral intensity across the band of interest must be known, in order to compensate for possible non-uniform source intensity.

The source calibration process includes collecting the background power spectrum without a sample volume in the optical; collecting the sample power spectrum; and then dividing (or forming a ratio of) the sample power spectrum by the background power spectrum to determine the sample intensity/background intensity, or transmission, for every frequency position reported by the apparatus. Customarily, the data is further processed by a logarithmic operation, i.e., determining the absorbance spectrum (ABS), as $$ABS = -\log_{10}(\text{sample/background}).$$

Once an absorbance spectrum has been determined, the disclosed apparatus and method may be used in industrial or environmental process monitoring to measure a thickness of a solid or liquid film or coating on another solid or liquid, for example.

Based on the general operation procedures describe above, the absorbance spectrum of a sample is obtained with the disclosed invention. The quantity of absorbance (ABS) can be expressed, in general, as follows:

$$ABS = A \times B \times C,$$

where A is the absorption coefficient of the absorbing functional groups present in the sample; B is the path length within the sample (thickness), and C is the concentration of the functional groups. This quantitative relation is widely known as "Beer's Law".

Concentration and thickness measurements can be made using a standard sample with known concentration C and known thickness B, to calculate the absorption coefficient A for any vibrational band shown by that sample. Once A is known for the absorption band, one then can use Beer's Law to measure either the concentration or the thickness.

For example, in a film processing line, if the material formulation is held constant, then the corresponding C and A values are also constant. In this case, one can use the disclosed invention to monitor the film thickness, since the absorbance level is directly proportional to B. On the other hand, in a semiconductor chemical vapor deposition (CVD) processing chamber, for example, the concentration of the gaseous species can be measured with the disclosed invention since A (a known species) and B (a fixed chamber size) are held constant, leaving the concentration to be determined as being directly proportional to the measured absorbance.

Orientation measurements are made in the following way. When non-polarized IR light is used in IR measurements, all functional groups with the matching vibration frequencies will cause absorption. However, when the incident IR light is linearly polarized so that only electromagnetic waves oscillating in a particular direction are passed, then only the functional groups having both matching frequencies and a dipole moment change in the same direction as the polarized light can absorb the incident light.

For randomly oriented samples, all dipole directions are equally sampled, and therefore no dependence on the polarization direction would be observed. On the other hand, for samples with preferred orientation caused by processing steps, there would be much stronger absorbance when the polarization direction matches that of the sample dipole change direction. By comparing the absorption spectra with polarized and non-polarized IR light, one can deduce to what extend the sample under study is oriented, and in which direction.

The polarization of infrared light is often accomplished with the use of a gold wire polarizer. This optical device may be composed of, for example, finely separated gold wires arranged in parallel on a IR transparent substrate, such as ZnS.

The quantitative relation between the polarization direction and the sample dipole direction is depicted as follows:

$$ABS_{Observed} \propto \cos(\Theta),$$

where $\Theta$ is the angle between the sample's dipole moment change direction during the vibration, and the polarization direction of the incident IR light. From the above relation, one can see that, when $\Theta = 90°$, there will be no absorption, even if the vibration frequency condition is satisfied.

INDUSTRIAL APPLICABILITY

The application and method of the disclosed invention has wide applicability to a variety of industrial and environmental processes.

Some of the applications include a method to measure the thickness, the chemical structure and orientation of coatings (solid, liquid, chemically bound, physically adsorbed) on solid surfaces, including but not limited to semiconductors, metals and dielectrics.

For example, in modern materials processing utilized in device manufacturing, subtle differences in the processed materials on a molecular level can determine the success or failure of a specific procedure. Molecular parameters such as crystalline order, chain orientation, and hydrogen bonding strength can have important effects on the functionality of the final devices. For example, liquid crystal displays used in notebook computers rely on the chain orientation of the polymer coating used on the glass templates to define the "off" orientation of the liquid crystal molecules which act as a light modulator. The orientation of such polymer chains, however, is produced by a "buffing" process during which a piece of velour cloth is used to rub the polymer-coated glass in a given direction in order to induce chain orientation. Although it is well known that the yield of a flat panel display manufacturing line is critically dependent on a successful buffing process, there is no monitoring process used during the various manufacturing stages that can assess the chain orientation induced by buffing before final assembly is completed. Hence glass templates with bad LC aligning properties are not removed from the assembly line until the manufacturing process is completed. The cost of discarding failed fully assembled displays is several times higher than that of removing polymer-coated-and-buffed glass plates with poor alignment properties. The main difficulty in realizing this more efficient quality control process is that there is no reliable detection method that can survive the aggressive operating conditions found in a manufacturing plant.

Process methods such as scanning probe microscopy and x-ray diffraction, for example, can be destructive in nature, requiring long data collection times and removal of samples from the production line. Consequently, the real-time statistics needed for a successful on-line process monitoring method cannot be achieved with these techniques. The disclosed apparatus and method can non-destructively monitor processes in real-time, for example, information about chain orientation of large area samples can be obtained in situ after the buffing process is completed.

The present inventors have been involved in the study of liquid crystal alignment using different organic, inorganic and polymer surfaces, and have shown that the ordering, orientation, morphology, and topography of the template surface plays an important role in the final LC orientation. This information will be readily accessible to the flat panel display industry with the use of the portable infrared spectrometer disclosed here.

An environmental application of IR spectroscopy in an aqueous environment, for example on a lake, river, or on the ocean could be detection and measurement of oil or other contaminants on the surface using reflected IR energy to determine the presence or absence of specific functional groups.

In addition, because the IR spectrometer is highly mobile, it may be used as a water pollution monitor, capable of operation in the field as discussed above. The spectral range offered in the disclosed spectrometer will cover the spectral features in the fingerprint region for most of the aromatic pollutants. Since the IR bands (1600–1750 cm$^{-1}$) assignable to water will not interfere with the pollutants' signal in this spectral range, bulk analysis of wastewater in the field is also possible with this instrument.

Another application is IR spectroscopy on thin films. Many of the optical, mechanical and aging properties of polymers are a direct function of the order, orientation, and morphological development, which occurs during processing. Ironically little, if any, understanding exists on the structural development of orientation and order at the time when polymers are formed into thin films. The ability to structurally characterize the nature of polymer chain organization by real-time IR spectroscopic methods would allow the optimization of processing protocols providing eventual control of the desired amount of crystallization and orientation relative to the direction of micro mechanical deformation. In many cases, this is simply manifested by specific IR bands which can be attributed to either trans or gauche bonds, and crystalline or amorphous material. Following both the intensity and the frequency of IR bands as processing (heating, stretching, cooling) of thin films occurs will allow us to follow the molecular development of orientation and crystal morphology as it occurs.

Although many studies on poly(ethylene) (PE) films and fibers have been done, the information provided is usually obtained both before processing, and after deformation, heating, etc., has been completed. Providing spectroscopic information in different spatial regions and in real-time is possible with the disclosed fiber optic IR instrument. Depending on the spectral range of the focal plane array chosen, it is possible to investigate the development of crystallinity using the 1460–1470 cm$^{-1}$ (doublet) $CH_2$ scissors vibration, and the 720–730 cm$^1$ (doublet) $CH_2$ rocking vibration, which are characteristic of the orthorhombic unit cell. Furthermore, since the transition moments of the $CH_2$ rocking components at 730 and 720 cm$^{-1}$ are parallel to the "a" and "b" axes of the unit cell ("c" is along the chain axis) respectively, it should also be possible to determine the extent of biaxial orientation which is introduced in the drawing process by following the relative intensities of the 730 and 720 cm$^{-1}$ bands in the polarized IR beam during processing.

In addition, since both sets of bands (rocking and scissors) are highly polarized perpendicular to the polymer chain axis, their intensity can also be used to provide information on axial orientation related to the direction of mechanical deformation. Likewise the CH stretching vibrations located at 2920 cm$^{-1}$ (asymmetric $CH_2$ stretch) and 2850 cm$^{-1}$ (symmetric $CH_2$ stretch) are strongly polarized out of the plane of the carbon backbone and in the plane of the carbon backbone respectively. Hence these vibrations can also be used to determine the extent of "a" and "b" axis orientation in biaxially oriented films.

Unlike Raman spectroscopy where the intensities depend on changes in polarizabilities, making the interpretation of induced orientation less straightforward, IR intensities depend on the change in dipole moment (for a particular vibrational mode), and hence provide a more direct assessment of chain orientation, provided the direction of the orientation of the change in dipole moment is known, relative to the polymer chain axis. In the case of PE, these are well known, and PE is an appropriate polymer on which to conduct IR spectroscopy.

Another application is to measure a series of poly(ester) thin films. Although a number of studies on poly(ethylene terephthalate) (PET) films pre-and post-processing have appeared in the literature, no studies on PET during processing have been reported. In addition, little work has appeared on structurally related poly(ethylenenaphthalate) (PEN). Since the primary commercial market for PEN is now specialty films, because of its improved (relative to PET) thermal and dielectric properties, an understanding of the effect of various processing parameters on properties would be both fundamentally important and timely.

In previous studies of PET after stretching, it has been shown that bands at 973 and 1041 $cm^{-1}$, previously assigned to trans and gauche conformations of the —$OCH_2CH_2O$— groups, show a considerable change in intensity (973 $cm^{-1}$ also shifts in frequency) after the application of stress. This suggests that stress transforms gauche bonds into trans, although this evidence alone did not indicate that the overall sample crystallinity had increased. This required the use of the 848 $cm^{-1}$ $CH_2$ rocking vibration characteristic of trans conformers in the crystalline regions which was also followed as a function of stress and found to increase as the 973 $cm^{-1}$ trans band increased.

Similar behavior was also observed for the 1386 $cm^{-1}$ $CH_2$ wagging mode which has also been observed to be characteristic of trans bonds in the crystalline regions of PET. Since the —$OCH_2CH_2O$— groups are common linkages between the aromatic groups in both polyester chains, monitoring the intensity and frequency changes of the 973, 1041, 848 and 1386 $cm^{-1}$ bands so as to understand the effect of processing parameters on the development of orientation, all trans content and crystallinity in both PET and PEN films. In addition, changes in crystallization and orientation in PET and PEN can also verified by following the CH stretching modes at 2870 and 2850 $cm^{-1}$ while orientation alone can be followed using the C=O overtone vibration at 3200 $cm^{-1}$.

Further industrial applications of the disclosed apparatus include: a method to measure and detect the thickness, either in transmission or reflection, the chemical structure and orientation of coatings/films (solid, liquid, chemically bound, physically adsorbed) on liquid surfaces, including but not limited to water, oil and other solvents;

A method to measure and detect the thickness, either in transmission or reflection, the chemical structure and orientation of oil on water including but not limited to environmental oil spills, polluted lakes, streams, rivers, etc.;

A method to measure the thickness, orientation and chemical structure of fluorocarbon materials, including but not limited to films, adsorbed gas, coatings on solid and liquid surfaces;

A method to measure the thickness, orientation and chemical structure of films electrochemically deposited on solid substrates, including but not limited to metals and semiconductors;

A method to measure the changes in thickness, orientation and chemical structure of films, either free-standing or supported on solid or liquid substrates, that have been chemically or physically degraded by heat, radiation or light;

A method to detect orientation in films either statically or "real-time" as they are being processed (stretched, crystallized, aligned are representative, but not limiting examples of processing);

A real-time method to measure the thickness, orientation, chemical structure and crystallization of films, either free-standing or supported on solid or liquid substrates;

A real-time method to measure and detect the chemical species present as a chemical reaction in the gaseous, liquid or solid state occurs;

A real-time method to measure and detect hazardous materials in the gaseous state, including but not limited to fumes in factory, laboratory, mining tunnel, storage room and battlefield;

A real-time method to monitor processes, including but not limited to those involving orientation, crystallization, melting, degradation, deposition and sublimation;

A monitoring method which can be deployed in environments with high mechanical noises, including but not limited to factory, mine, automobile, aircraft or spacecraft;

A monitoring method which can be deployed with infrared telescopic optics and serve as a remote-sensing platform;

A monitoring method which can be deployed with infrared microscopic optics and perform real-time infrared microscopic sampling;

A monitoring method, which can be deployed with infrared optical fibers to perform medical endoscopic detection.

EXPERIMENTAL RESULTS

Based on a preliminary ray-tracing calculation with the refractive index information shown in FIG. 5, a 67.5° Pellin-Broca prism made of ZnSe operating in the "short-side entrance" geometry at approximately the Brewster angle ($\theta_B$ of ZnSe~67°) will give angular dispersion of about 6° between the 3 and 13 $\mu$m wavelength beams. The on-chip spatial separation between the different wavelengths is determined by the focusing optics used, the size of the Pellin-Broca prism, and the f-number of the system. A span of between 500 to 1000 $cm^{-1}$ of the spectral range may be focused onto the FPA horizontally (256, 320, etc. pixels). Given the number of pixels in the FPA along the dispersion direction of the optical beam, the maximum resolution is about 5 $cm^{-1}$. However, using different optical components, such as a finer grooved grating, for example, a resolution of better than 5 $cm^{-1}$ is achievable for this spectrometer.

In order to assess the performance of the FPA-IR spectrograph, a spectrum of hexadecane ($C_{16}H_{34}$) was obtained in the CH stretching region in 10 $\mu$s and is shown in the FIG. 6. For this experiment the 3–5 $\mu$m FPA was used in conjunction with a 300 groove/mm IR grating. The various sections "A", "B", and "C" of FIG. 6 show various levels of signal integration, and improvement in SNR available from the use of multiple rows, and multiple acquisition frames, or periods. The right-hand side of FIG. 6 indicates the noise levels associated with these various approaches.

For comparison, as shown on the right-hand side of FIG. 7, IR spectra of hexadecane were also obtained using a conventional FTIR instrument using 16 $cm^{-1}$, 8 $cm^{-1}$, and 4 $cm^{-1}$ resolution. The methyl stretch at 2875 $cm^{-1}$, observed in all three spectra, can be used as an indication of the instrument's resolution. This weak band is found on the high frequency side of the much stronger symmetric $CH_2$ stretch at 2850 $cm^{-1}$. The methyl stretch in the FPA-IR spectrum is less resolved than that in the 4 $cm^{-1}$ resolution FTIR spectrum, but more resolved than that in the 8 $cm^{-1}$ resolution FTIR spectrum.

Thus this is a clear proof that the design of the disclosed FPA-IR spectrometer works at a resolution in the range of 4–8 $cm^{-1}$. It significantly improves the collection time (for similar SNR spectra) from minutes to microseconds, and hence allows dynamic processes to be investigated. Further, improvement in system resolution and throughput can be achieved by optimizing various components, while binning of the detector's vertical pixels improves the SNR in weakly absorbing systems.

Although discussion of a preferred embodiment of the present invention has been directed to determining IR spectral information, the method and system of the present invention is not limited merely to such a narrow implementation. For example, the present invention may also be applicable to the above-discussed industrial and environmental processes, and may further be incorporated into a control system in a batch production line to control one or more physical attributes, such as a polymer film thickness, or in semiconductor processing, for example.

It will be obvious that the present invention may be varied in many ways. For example, the specific optical components may be varied, as may their particular location with respect to the sample volume. Such variations are not to be regarded as a departure from the spirit and scope of the invention, and all such modifications as would be obvious to one skilled in the art are intended to be included within the scope of the following claims. The breadth and scope of the present invention is therefore limited only by the scope of the appended claims and their equivalents.

What is claimed is:

1. An apparatus for determining IR spectral information of a sample in a sample volume, comprising:
   an IR light source;
   a sampling accessory for positioning the sample volume in an optical path;
   an adjustable aperture in the optical path;
   an optically dispersive element in the optical path,
   wherein at least a portion of an emission from the IR light source is passed through the sample along the optical path, said at least a portion of an emission interacting with the optically dispersive element to form a dispersed light beam; and
   an IR detector having a plurality of detection elements therein arranged at least along a dispersion direction of the dispersed light beam,
   wherein the IR detector detects the dispersed light beam and provides an output which determines the IR spectral information of the sample, and
   wherein the apparatus is capable of determining the IR spectral information using no moving parts dining operation.

2. The apparatus of claim 1, wherein the optically dispersive element is a diffraction grating.

3. The apparatus of chim 1, wherein the optically dispersive element as a prism.

4. The apparatus of claim 3, wherein the optically dispersive element is a Pellin-Broca prism.

5. The apparatus of claim 3, wherein the prism is substantially transparent to IR wavelengths.

6. The apparatus of claim 3, wherein the prism comprises ZnSe.

7. The apparatus of claim 1, wherein the optically dispersive element is adjustable, and a range of wavelengths in the dispersed light beam projected onto the IR detector is determined by adjusting an angle of incidence between the at least a portion of an emission from the IR light source and a surface of the optically dispersive element.

8. The apparatus of claim 1, wherein the adjustable aperture is a slit having at least an adjustable width.

9. The apparatus of claim 1, wherein the adjustable aperture is an adjustable iris.

10. The apparatus of claim 1, wherein the IR detector comprises a plurality of detection elements arranged in a plurality of rows.

11. The apparatus of claim 1, wherein the IR detector is a focal plane array.

12. The apparatus of claim 11, wherein the focal plane array comprises InSb.

13. The apparatus of claim 11, wherein the focal plane array is an microbolometer focal plane array.

14. The apparatus of claim 11, wherein the focal plane array comprises MCT.

15. The apparatus of claim 11, wherein a plurality of focal plane array pixel outputs corresponding to at least one of a plurality of wavelengths contained in the dispersed light beam are summed together to improve a signal-to-noise ratio of a signal representing an amplitude of the at leant one of a plurality of wavelengths.

16. The apparatus of claim 11, wherein the dispersed light beam is projected onto the focal plane array such that a row direction along the focal plane array is essentially aligned with the dispersion direction of the dispersed light beam, and wherein each column of the focal plane array corresponds to an associated wavelength of light in the dispersed light beam.

17. The apparatus of claim 16, wherein the dispersed light beam is projected onto the focal plane array such that a plurality of rows is illuminated by the dispersed light beam.

18. The apparatus of claim 17, wherein an output from one pixel in each of the plurality of rows are added together along one column of the focal plane array to improve a signal-to-noise ratio of a signal representing en amplitude of the associated wavelength of light.

19. The apparatus of claim 18, wherein pixel outputs are added together along each of a plurality of columns of the focal plane array.

20. The apparatus of claim 1, wherein the output from the IR detector includes a plurality of summed detector outputs at each of a plurality of wavelengths contained in the dispersed light beam,
   wherein the plurality of summed detector outputs improve a signal-to-noise ratio of signals representing associated amplitudes of said each of the plurality of wavelengths.

21. The apparatus of claim 1, wherein the IR detector detects light having a wavelength at least in a mid-IR band.

22. The apparatus of claim 1, wherein said sampling accessory is a sample holder.

23. The apparatus of claim 1, wherein said optical path includes at least one optical fiber.

24. The apparatus of claim 23, wherein said at least one optical fiber is a multimode fiber.

25. The apparatus of claim 23, wherein said at least one optical fiber propagates light in a mid-IR band.

26. The apparatus of claim 1, wherein said sampling accessory is configured to provide an optical density of the sample which is adequate for detection of an IR absorption phenomena within said sample volume.

27. The apparatus of claim 1, further comprising:
   a display for displaying an IR spectrograph; and
   means for controlling the IR detector and the displays.

28. The apparatus of claim 27, wherein the means for controlling the IR detector and the display includes a personal computer.

29. The apparatus of claim 1, wherein IR detector comprises an IR camera.

30. The apparatus of claim 1, further comprising a personal computer operatively connected to said IR detector, wherein the personal computer processes the IR detector output to identify one or more chemical functional groups in the sample.

31. The apparatus of claim 30, further comprising an alarm that is activated based upon a detection of one or more signature chemical functional groups in the sample.

32. An apparatus for determining IR spectral information of a sample in a sample volume, comprising:

an IR light source;

a sampling accessory for positioning the sample volume in an optical path;

an optically dispersive element in the optical path, wherein at least a portion of an emission from the IR light source is passed through the sample along the optical path, said at least a portion of an emission interacting with the optically dispersive element to form a dispersed light beam;

an IR detector having a plurality of detection elements therein arranged at least along a dispersion direction of the dispersed light beam;

wherein the IR detector detects the dispersed light beam and provides an output which determines the IR spectral information of the sample, wherein the apparatus is capable of determining the IR spectral information using no moving parts during operation; and a plurality of sampling accessories each positioning at least one different sample volume, wherein the apparatus simultaneously determines IR spectral information of each of the at least one different sample volumes.

33. An apparatus for determining IR spectral information of a sample in a sample volume, comprising:

an IR light source;

a sampling accessory for positioning the sample volume in an optical path;

an optically dispersive element in the optical path, wherein at least a portion of an emission from the IR light source is passed through the sample along the optical path, said at least a portion of an emission interacting with the optically dispersive element to form a dispersed light beam;

an IR detector having a plurality of detection elements therein arranged at least along a dispersion direction of the dispersed light beam, wherein the IR detector detects the dispersed light beam and provides an output which determines the IR spectral information of the sample, wherein the apparatus is capable of determining their spectral information using no moving parts during operation; and a plurality of optically dispersive elements for forming a plurality of dispersed light beams each corresponding to a different sample.

34. A real-time, non-interferometric apparatus using IR absorption phenomena and no moving parts during operation to perform chemical analysis in one or more sample volumes, the apparatus comprising:

a broadband light source;

at least one sampling accessory for positioning the one or more sample volumes so that at least a portion of light emitted from the broadband light source passes through each of the one or more sample volumes;

adjustable means for optically dispersing the at least a portion of light passed through each of the one or more sample volumes to obtain one or more corresponding dispersed sample beams;

a two-dimensional IR detector array having a plurality of detector elements arranged in rows and columns, stationary, non-rotating optical coupling means for coupling the one or more corresponding dispersed sample beams onto the two-dimensional IR detector array; and processor means for controlling the two-dimensional IR detector array and providing non-interferometric chemical analysis of said one or more samples based at least upon an IR absorption spectrum in one or more particular wavelength regions, wherein each of the one or more corresponding dispersed sample beams are simultaneously projected on multiple rows in a different area of the two-dimensional IR detector array, and corresponding column detector elements in each of the multiple rows are added together within each different area of the two-dimensional IR detector array to determine an intensity of an IR spectral component at a particular wavelength in real time, and wherein a signal-to-noise ratio of a signal representing the intensity of the IR spectral component at the particular wavelength is increased by adding the corresponding column detector elements in each of the multiple rows.

35. The apparatus of claim 34, wherein the adjustable means for optically dispersing the at least a portion of light passed through each of the one or more samples is a diffraction grating having an adjustable angle of incidence with respect to incident light impinging thereon.

36. The apparatus of claim 34, wherein the adjustable means for optically dispersing the at least a portion of light passed through each of the one or more samples is a Pellin-Broca prism having an adjustable angle of incidence with respect to incident light projected thereon.

37. The apparatus of claim 34, wherein the optical coupling means includes direct lens coupling.

38. The apparatus of claim 34, wherein the optical coupling means includes one or more optical fibers.

39. The apparatus of claim 34, wherein the two-dimensional IR detector array is an InSb focal plane array.

40. The apparatus of claim 34, wherein the two-dimensional IR detector array is a microbolometer focal plane array.

41. The apparatus of claim 34, wherein the two-dimensional IR detector includes MCT.

42. The apparatus of claim 34, wherein the processor means is a personal computer.

43. The apparatus of claim 34, wherein said adjustable means for optically dispersing the at least a portion of light passed through each of the one or more samples is adjusted to tune a wavelength range of said one or more corresponding dispersed sample beams.

44. The real-time, non-interferometric apparatus of claim 34, wherein the stationary optical coupling means comprises an adjustable aperture in an optical path.

45. A method of determining an IR spectrum of at least one sample in a sample volume using a non-interferometric apparatus, the method comprising:

providing an IR source;

positioning the at least one sample volume in an optical path;

passing at least a portion of an emission of the IR source through the at least one sample volume and into the optical path;

optically dispersing the at least a portion of an emission of the IR source to form a dispersed IR light beam;

simultaneously detecting each spectral component of the dispersed IR light beam using a plurality of detectors arranged two-dimensionally in rows and columns;

non-interferometrically determining the IR spectrum of the at least one sample by evaluating an output from each detector in at least two rows of detectors, wherein each column of detectors represents a wavelength contained within the dispersed IR light beam; and maintaining fixed relative positions of all components of the non-interferometric apparatus at least during the step of simultaneously detecting each spectral component of the dispersed IR light beam.

46. The method of claim 45, further comprising adjusting the optical dispersion of the at least a portion of an emission of the IR source to control a range of wavelengths in the dispersed IR light beam.

47. The method of claim 45, further comprising increasing a signal-to-noise ratio by co-adding a plurality of detector outputs in each of the columns.

48. The method of claim 45, further comprising increasing a signal-to-noise ratio by co-adding a plurality of detector outputs obtained during more than one acquisition period of the plurality of detectors.

49. The method of claim 45, further comprising:

evaluating a spectrum of the IR source; and correcting a portion of a plurality of outputs of the plurality of detectors to account for the spectrum of the IR source.

50. The method of claim 49, further comprising adjusting at least one dimension of an optical opening located between the IR source and the at least one sample to adjust a resolution of the non-interferometric apparatus.

51. The method of claim 45, further comprising maintaining all components of the apparatus in a stationary position relative to each other at least during said steps of passing, dispersing, detecting, and determining.

52. The method of claim 45 further comprising processing the determined ER spectrum to identify one or more molecular functional groups in the at least one sample.

53. The method of claim 45 further comprising:

processing the determined IR spectrum to identify one or more signature functional groups in the at least one sample; and enabling an alarm if one or more of said one or more signature functional groups are found in the at least one sample.

54. The method of claim 45, further comprising providing an adjustable aperture in the optical path.

55. A method of determining an IR spectrum of at least one sample in a sample volume using a non-interferometric apparatus, the method comprising:

providing an IR source;

positioning the at least one sample volume in an optical path;

passing at least a portion of an emission of the IR source through the at least one sample volume and into the optical path;

optically dispersing the at leant a portion of an emission of the IR source to form a dispersed IR light beam;

detecting the dispersed IR light beam using a plurality of detection arranged two-dimensionally in rows and columns:

non-interferometrically determining the IR spectrum of the at least one sample by evaluating an output from each detector in at least two rows of detectors, wherein each column of detectors represents a wavelength contained within the dispersed IR light beam; and simultaneously analyzing multiple samples in at least two sample volumes.

56. A method of determining an IR spectrum of at least one sample in a sample volume using a non-interferometric apparatus, the method comprising:

providing an IR source;

positioning the at least one sample volume in an optical path;

passing at least a portion of an emission of the IR source through the at least one sample volume and into the optical path;

optically dispersing the at least a portion of an emission of the IR source to form a dispersed IR light beam;

detecting the dispersed IR light beam using a plurality of detectors arranged two-dimensionally in rows and columns;

non-interferometrically determining the IR spectrum of the at least one sample by evaluating an output from each detector in at least two rows of detectors, wherein each column of detectors represents a wavelength contained within the dispersed IR light beam; and simultaneously presenting a plurality of spectral images to the plurality of detector outputs, wherein each of the plurality of spectral images is projected onto a different area of the plurality of detector outputs.

57. A method of determining an IR spectrum of at least one sample in at least one sample volume using IR absorption in a non-interferometric apparatus, the apparatus including a broadband IR source; at least one sample accessory for positioning the at least one sample volume; an optically dispersive element; and a two-dimensional IR detector having a plurality of detection elements arranged in columns and rows, the method comprising:

projecting at least a portion of an emission of the broadband IR source into the at least one sample volume;

coupling a light beam transmitted through the at least one sample volume to the optically dispersive element;

forming a dispersed IR light beam;

simultaneously detecting each spectral component of the dispersed IR light beam using the two-dimensional IR detector while maintaining all components of the apparatus in relatively fixed positions with respect to each other; and non-interferometrically determining the IR spectrum of the at least one sample by simultaneously evaluating an output from each detector in a plurality of rows of detectors, wherein each column of detectors represents a wavelength contained within the dispersed IR light beam.

58. The method of claim 57, further comprising maintaining the broadband IR source, the optically dispersive element, and the two-dimensional IR detector motionless at least with respect to each other at least during said steps of projecting, coupling, forming, detecting, and determining.

59. The method of claim 57, further comprising increasing a signal-to-noise ratio by co-adding a plurality of detector outputs in each of the columns.

60. The method of claim 57, further comprising increasing a signal-to-noise ratio by co-adding a plurality of detector outputs obtained during more than one acquisition period of the two-dimensional IR detector.

61. The method of claim 57, wherein said coupling step includes direct lens coupling.

62. The method of claim 57, wherein said coupling step includes fiber optic coupling.

63. The method of claim 62, wherein said fiber optic coupling at least includes coupling the dispersed IR light beam into the two-dimensional IR detector from the at least one sample volume which is remotely located a substantial distance from the two-dimensional IR detector and the non-interferometric apparatus.

64. The method of claim 63, further comprising fiber optically coupling the at least a portion of the emission of the broadband IR source into the at least one sample volume.

65. The method of claim 57, further comprising simultaneously projecting multiple spectral images onto the two-dimensional IR detector,
   wherein each of the multiple spectral images is projected onto a different area of the two-dimensional IR detector,
   each of the multiple spectral images representing an IR spectrum of a corresponding sample.

66. The method of claim 57, further comprising processing the determined IR spectrum to detect the presence of one or more molecular functional coups.

67. The method of claim 57, further comprising enabling an alarm if the determined IR spectrum includes one or more signature functional groups.

68. The method of claim 57, further comprising detecting, from said IR spectrum, a chemical species in real-time in any of a gaseous, a liquid, and a solid state.

69. The method of claim 68, wherein said detecting a chemical species in real time includes detecting a chemical or a biological warfare agent.

70. The method of claim 68, wherein said detecting a chemical species in real time includes measuring and detecting a gaseous hazardous material, wherein said gaseous hazardous material includes hazardous fumes or vapors.

71. The method of claim 57, further comprising determining, from the IR spectrum, at least one physical attribute of the at least one sample.

72. The method of claim 71, wherein the at least one physical attribute is continuously determined essentially in real-time.

73. The method of claim 71, wherein said determining at least one physical attribute includes measuring at least one of a thickness, a chemical structure, and an orientation of a coating on a solid surface, wherein said solid surface includes at least one of a semiconductor, a metal, and a dielectric.

74. The method of claim 71, wherein said determining at least one physical attribute includes measuring a thickness, in either a transmission or a reflection mode, of a film on a liquid surface.

75. The method of claim 74, further comprising measuring the thickness of an oil film on a water surface.

76. The method of claim 71, wherein said determining at least one physical attribute includes detecting and measuring at least one of a thickness, a concentration, and a chemical structure of a fluorocarbon material.

77. The method of claim 71, wherein said determining at least one physical attribute includes measuring and detecting at least one of a thickness, an orientation, and a chemical structure of an film on a solid substrate.

78. The method of claim 71, wherein said determining at least one physical attribute includes measuring and detecting at least one of a thickness, an orientation, and a chemical structure of an electrochemically deposited film on a solid substrate including a semiconductor.

79. The method of claim 71, wherein said determining at least one physical attribute includes measuring and detecting at least one of a thickness, an orientation, and a chemical structure of a film that has been chemically or physically degraded by heat, radiation or light.

80. The method of claim 71, wherein said determining at least one physical attribute includes measuring a thickness of a film in real-time.

81. The method of claim 70, wherein said determining at least one physical attribute includes measuring and detecting at least one of a thickness, an orientation, a chemical structure, and a crystallization of a film.

82. The method of claim 57, wherein said coupling step further comprises coupling the light beam transmitted through the at least one sample volume through an IR telescope.

83. The method of claim 57, wherein said coupling step further comprises coupling the light beam transmitted through the at least one sample volume through an IR microscope.

84. The method of claim 57, wherein said coupling step further comprises coupling the light beam transmitted through the at least one sample volume through an endoscope.

85. The method of claim 57, wherein said step of coupling a light beam transmitted through the at least one sample volume to the optically dispersive element comprises providing a variable aperture in an optical path.

86. A method of determining an IR spectrum of at least one sample in at least one sample volume using IR absorption in a non-interferometric apparatus, the apparatus including a broadband IR source; at least one sample accessory for positioning the at least one sample volume; an optically dispersive element; and a two-dimensional IR detector having a plurality of detection elements arranged in columns and rows, the method comprising:
   projecting at least a portion of an emission of the broadband IR source into the at least one sample volume;
   coupling a light beam transmitted through the at least one sample volume to the optically dispersive element;
   forming a dispersed IR light beam;
   simultaneously detecting each spectral component of the dispersed IR light beam using the two-dimensional IR detector; and
   non-interferometrically determining the IR spectrum of the at least one sample by simultaneously evaluating an output from each detector in a plurality of rows of detectors,
   wherein each column of detectors represents a wavelength contained within the dispersed IR light beam;
   determining, from the IR spectrum, at least one physical attribute of the at least one sample; and
   based on said at least one physical attribute, controlling at least one of a stretching, a crystallizing, and an aligning process.

87. An apparatus for collecting, processing, and displaying real-time IR spectral information of a material illuminated by an IR light source, comprising:
   an optically dispersive element;
   an IR focal plane array; and
   light coupling means for coupling an IR signal resulting from an IR absorption interaction within the illuminated material to the IR focal plane array;
   processing means for processing an output of the IR focal plane array and simultaneously determining each spectral component of the IR spectral information; and
   display means for displaying the IR spectral information.

88. The apparatus of claim 87, wherein said IR signal resulting from an IR absorption interaction within the illuminated material is reflected from the material.

89. The apparatus of claim 87, wherein said IR signal resulting from an IR absorption interaction within the illuminated material is transmitted through the material.

90. The apparatus of claim 87, wherein said light coupling means includes fiber optical coupling.

91. The apparatus of claim 87, wherein said processing means analyzes the IR focal plane output and enables an alarm if one or more specific functional groups is detected.

92. An apparatus for collecting, processing, and displaying IR spectral information of a material illuminated by an IR light source, comprising:

an optically dispersive element;

an IR focal plane array; and light coupling means for coupling an IR signal resulting from an IR absorption interaction within the illuminated material to the IR focal plane array;

processing means for processing an output of the IR focal plane array and determining the IR spectral information; and display means for displaying the IR spectral information, wherein said light coupling means includes a polarizing element.

93. An apparatus for determining IR spectral information of a sample in a sample volume, comprising:

an IR light source;

a sampling accessory for positioning the sample volume in an optical path;

an optically dispersive element in the optical path, wherein at least a portion of an emission from the IR light source is passed through the sample along the optical path, said at least a portion of an emission interacting with the optically dispersive element to form a dispersed light beam; and an IR detector having a plurality of detection elements therein arranged at least along a dispersion direction of the dispersed light beam; and processor means for receiving a real-time output from the IR detector and processing the real-time output entirely within a frequency or wavelength domain, wherein the processor means simultaneously determines each spectral component of the IR spectral information of the sample, wherein the apparatus is capable of determining the IR spectral information using no moving parts during operation.

* * * * *